United States Patent
Spreitzer et al.

(10) Patent No.: US 6,509,507 B2
(45) Date of Patent: Jan. 21, 2003

(54) POLYMERIZABLE BIARYLS, PROCESS FOR THEIR PREPARATION AND THEIR USE

(75) Inventors: Hubert Spreitzer, Frankfurt (DE); Willi Kreuder, Mainz (DE); Heinrich Becker, Glashütten (DE); Jochen Krause, Frankfurt (DE)

(73) Assignee: Aventis Research & Technologies GmbH & Co. KG, Frankfurt am Main (DE)

( * ) Notice: Subject to any disclaimer, the term of this patent is extended or adjusted under 35 U.S.C. 154(b) by 0 days.

(21) Appl. No.: 09/981,866

(22) Filed: Oct. 16, 2001

(65) Prior Publication Data

US 2002/0087030 A1 Jul. 4, 2002

Related U.S. Application Data

(62) Division of application No. 09/319,606, filed as application No. PCT/EP97/06830 on Dec. 8, 1997, now Pat. No. 6,323,373.

(30) Foreign Application Priority Data

Dec. 11, 1996 (DE) .......................................... 196 51 439

(51) Int. Cl.[7] .......................... C07C 47/52; C07C 45/00; C07C 22/00; C08E 2/00

(52) U.S. Cl. ........................ 568/425; 568/426; 568/441; 568/442; 568/630; 568/715; 570/182; 570/183; 560/56; 560/64; 560/76; 560/78; 526/217; 526/218.1; 526/220; 526/236; 526/265; 526/270; 526/293; 428/917

(58) Field of Search ................................ 568/425, 426, 568/441, 442, 630, 715; 570/182, 183; 560/56, 64, 76, 78; 526/217, 218.1, 220, 236, 265, 270, 293; 428/917

(56) References Cited

FOREIGN PATENT DOCUMENTS

WO    WO 90/13148    11/1990

*Primary Examiner*—Sreeni Padmanabhan
(74) *Attorney, Agent, or Firm*—Frommer Lawrence & Haug LLP

(57) ABSTRACT

A process for preparing polymerizable biaryl derivatives comprises reacting an aromatic comprising a 6-membered ring which bears ester or benzylic OH groups in the 1,4 position with a second aromatic in a palladium-catalyzed cross-coupling reaction to give a biaryl and converting the ester or benzylic OH groups into polymerizable groups in one or more steps. The biaryls obtained are suitable for preparing polymers which are used as electroluminescence materials.

17 Claims, 3 Drawing Sheets

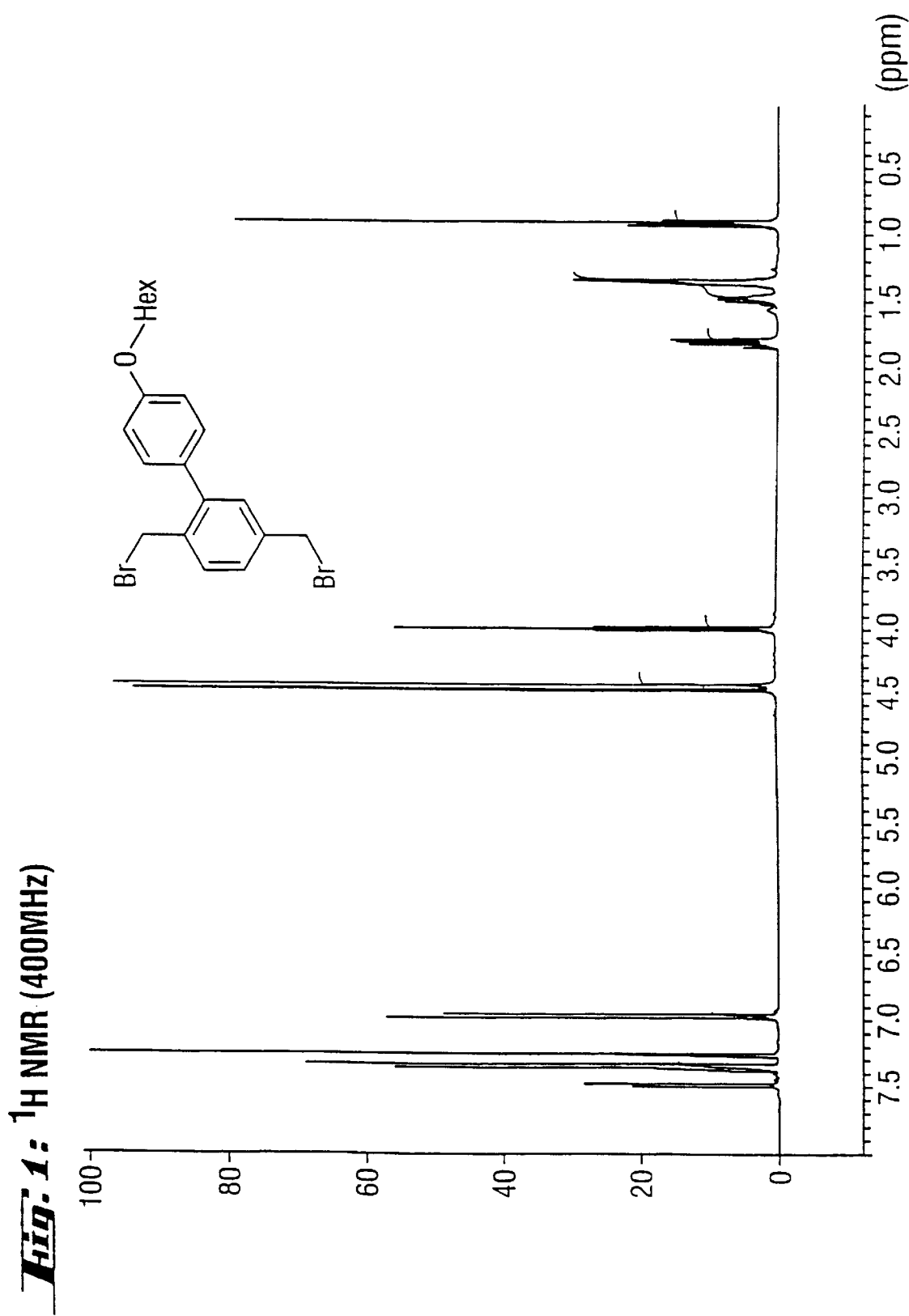
Fig. 1: ¹H NMR (400MHz)

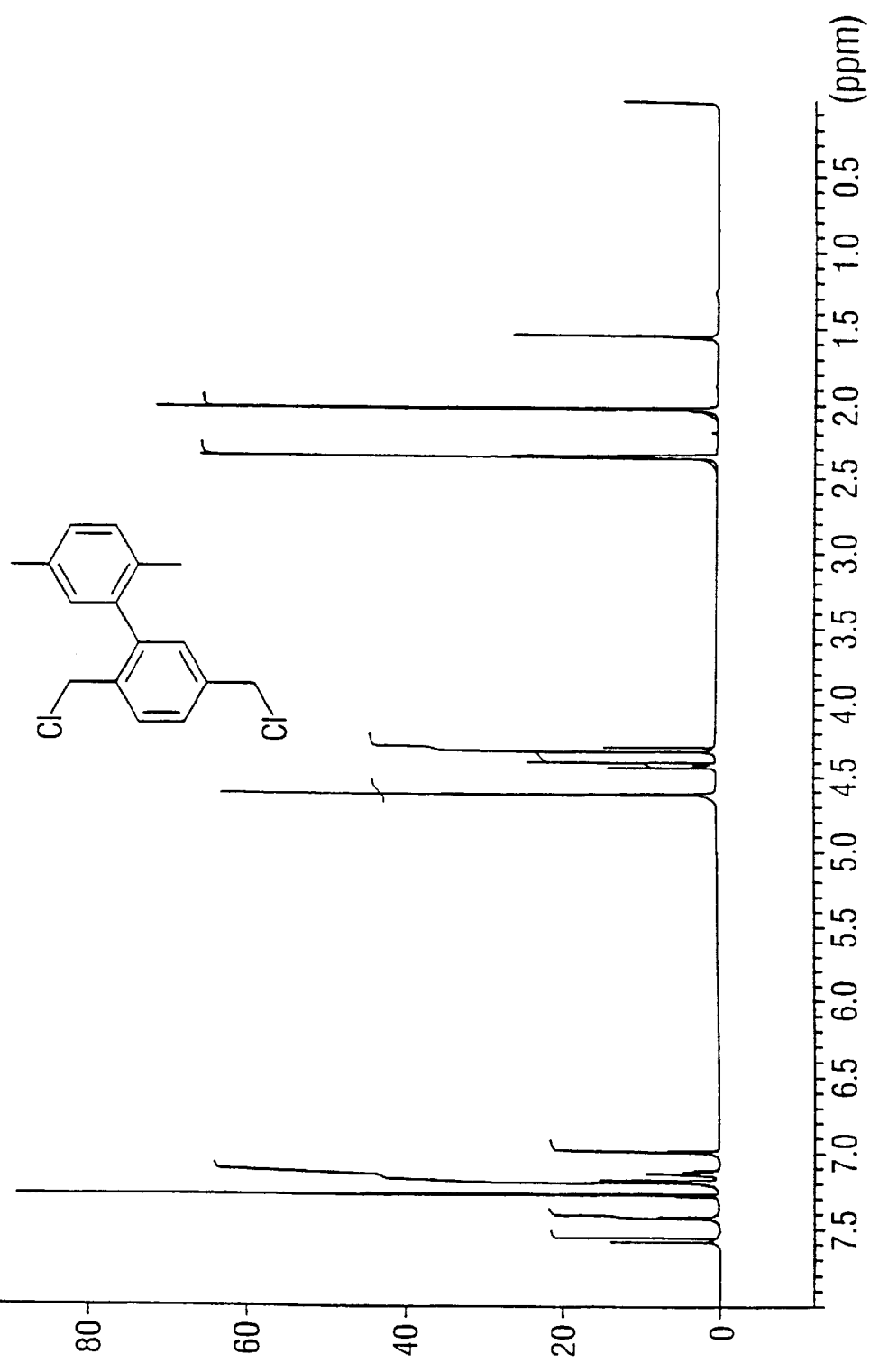
Fig. 2: ¹H NMR (400MHz)

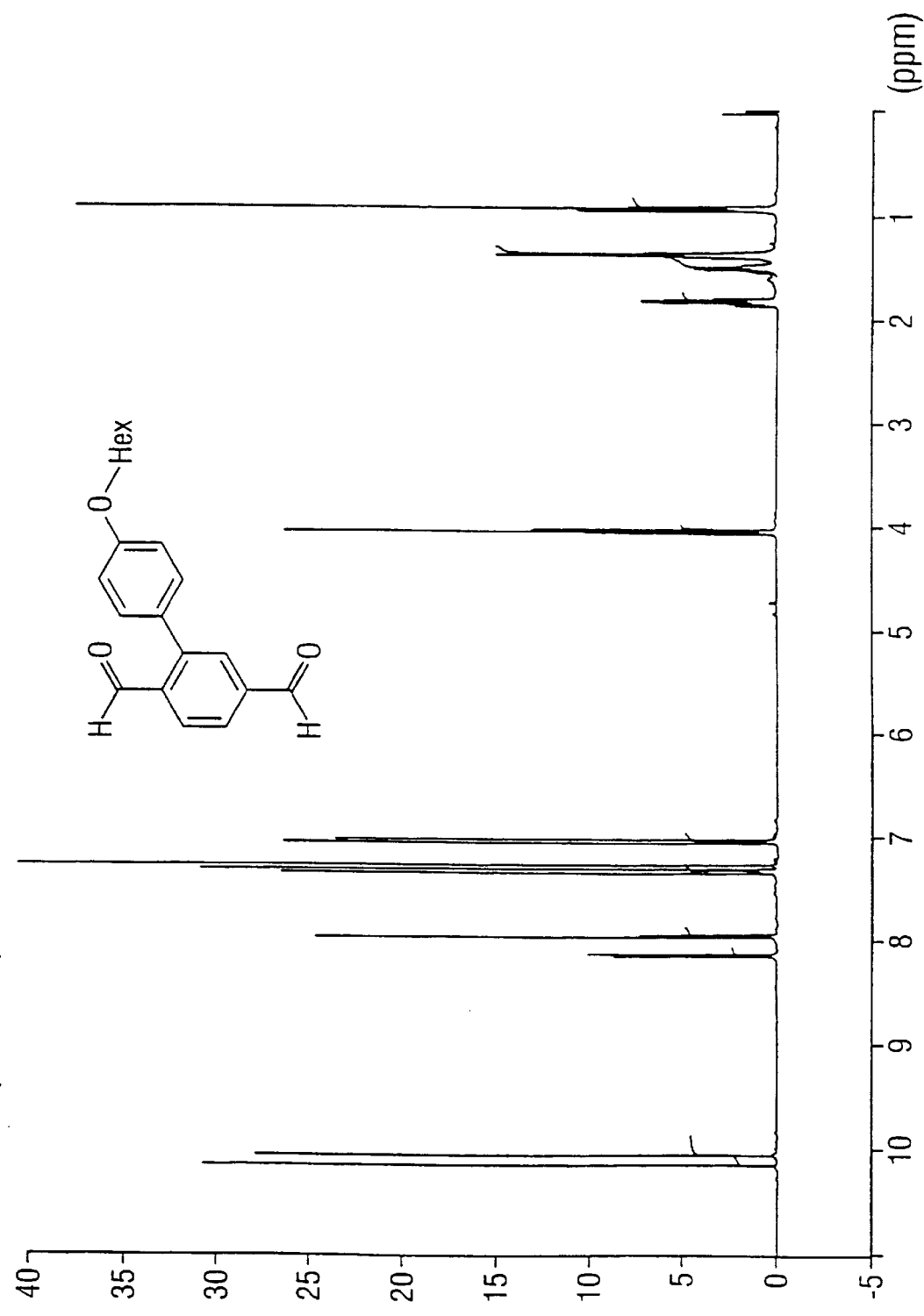
Fig. 3: ¹H NMR (400MHz)

POLYMERIZABLE BIARYLS, PROCESS FOR THEIR PREPARATION AND THEIR USE

RELATED APPLICATIONS

This application is a divisional of application U.S. Ser. No. 09/319,606, filed Jun. 9, 1999 herein incorporated by reference, which in turn is filed pursuant to 35 U.S.C. § 371 from PCT/EP97/06830, filed Dec. 8, 1997, which in turn claim priority to German application 19651439.8, filed Dec. 11, 1996.

Derivatives of poly(p-phenylenevinylene) have been known for some time as electroluminescence (EL) materials (see, for example, WO-A 90/13148). If the phenylene group in these polymers is substituted by one or more further aryl radicals, EL materials having a very special property spectrum, which are particularly suitable for generating green electroluminescence, are obtained. Starting compounds for such polymers are biaryl monomers which have two groups capable of polymerization, e.g. $CH_2Br$, present on one ring in the 1,4 positions.

In order to be able to prepare polymers having properties which are useful in practice in EL displays, the appropriate monomers are required in extraordinarily high purity. In addition, a requirement of industrial use is that an appropriate purity can be achieved in as few as possible simple and inexpensive steps.

Since, in addition, the development of electroluminescence materials, particularly those based on polymers, can in no way be regarded as concluded, the manufacturers of lighting and display devices are still interested in a wide variety of electroluminescence materials for such devices.

Industrial practice therefore needs, in, particular, a broad range of monomers to be able to be prepared by one synthetic method.

The prior art discloses the introduction of groups capable of polymerization into a biaryl by means of electrophilic substitution (cf., for example, G. Subramaniam et al., Synthesis, 1992, 1232 and v. Braun, Chem. Ber. 1937, 70, 979).

However, this route is not generally applicable, since the substitution usually takes place on both aryl systems, which requires at least a complicated separation of the various products.

The bromination of 4,4"-dihexyloxy-2',5'-dimethyl-p-terphenyl using N-bromosuccinimide has been described by J. Andersch et al., J. Chem. Soc. Commun. 1995, 107. However, bromination occurs here not only on the methyl groups but also one of the alkoxy chains (see Comparative Experiment V2 and K. L. Platt and F. Setiabudi, J. Chem. Soc. Perkin Trans. 1, 1992, 2005).

W. E. Bachmann and N. C. Denno, J. Am. Chem. Soc. 1949, 71, 3062, describe the synthesis of biaryl derivatives by 4+2 cycloaddition of a styrene to a diene-1,6-dicarboxylic acid derivative and subsequent dehydrogenation of the six-membered ring formed to give the aromatic. A disadvantage here is, apart from price and availability of the starting compounds, the fact that the conditions of the dehydrogenation reaction are not tolerated by all functional groups and the substitution pattern is therefore considerably restricted. There was therefore a further need for a general synthetic method which meets the abovementioned requirements. It has now been found that functionalized aryl-1,4-bismethanols and -biscarboxylic esters represent widely and simply accessible starting materials which can easily be converted in high purity into the desired monomers by the specific reaction sequence comprising palladium-catalyzed coupling with a second aryl component and conversion of the alcohol or ester functions into groups suitable for polymerization.

The invention accordingly provides a process for preparing a polymerizable biaryl derivative of the formula (I),

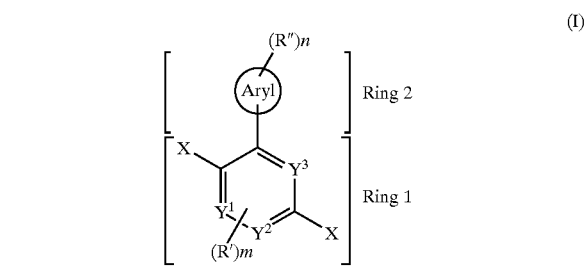

where the symbols and indices have the following meanings:

X: $-CH_2Z$, $-CHO$;

$Y^1$, $Y^2$, $Y^3$: identical or different, CH, N;

Z: identical or different, I, Cl, Br, CN, SCN, NCO, $PO(OR^1)_2$, $PO(R^2)_2$, $P(R^3)_3{}^+A^-$;

Aryl: an aryl group having from 4 to 14 carbon atoms;

R', R": identical or different, CN, F, Cl, a straight-chain or branched or cyclic alkyl or alkoxy group having from 1 to 20 carbon atoms, where one or more nonadjacent $CH_2$ groups can also be replaced by $-O-$, $-S-$, $-CO-$, $-COO-$, $-O-CO-$, $-NR_4-$, $-(NR^5R^6)^+-A^-$ or $-CONR^7-$ and one or more H atoms can be replaced by F, or an aryl group having from 4 to 14 carbon atoms which may be substituted by one or more nonaromatic radicals R';

$R^1$, $R^2$, $R^3$, $R^4$, $R^5$, $R^6$, $R^7$: identical or different, aliphatic or aromatic hydrocarbon radicals having from 1 to 20 carbon atoms, where $R^4$ to $R^7$ can also be hydrogen;

$A^\ominus$: a singly charged anion or its equivalent;

m: 0, 1 or 2;

n: 1, 2, 3, 4 or 5;

which comprises

A. reacting two aryl derivatives of the formulae (II) and (III),

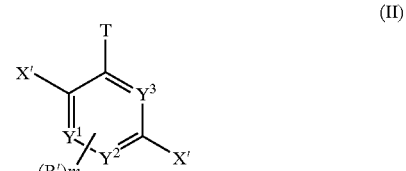

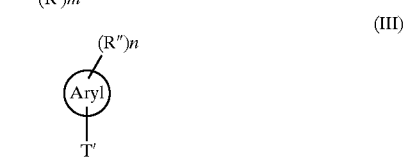

in an inert solvent in the presence of a palladium catalyst at a temperature in the range from 0° C. to 200° C. to give an intermediate of the formula (IV)

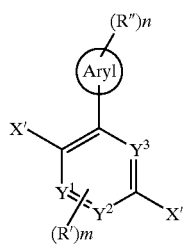

(IV)

where the symbols and indices have the meanings given in formula (I) and X': $CH_2OH$ or $COOR^8$;

one of the groups T, T': Cl, Br, I or a perfluoroalkylsulfonate radical, preferably having from 1 to 12 carbon atoms, and the other group T, T': $SnR_3$, $BQ_1Q_2$, where $Q_1$, $Q_2$ are identical or different and are each —OH, $C_1$–$C_4$-alkoxy, $C_1$–$C_4$-alkyl, phenyl which may bear $C_1$–$C_4$-alkyl, $C_1$–$C_4$-alkoxy or halogen groups as substitutents, or halogen or $Q_1$ and $Q_2$ together form a $C_1$–$C_4$-alkylenedioxy group which may be substituted by one or two $C_1$–$C_4$-alkyl groups; and $R^8$ are identical or different and are each H or a straight-chain or branched alkyl group having from 1 to 12 carbon atoms;

B. if the group X' in the intermediate of the formula (IV) is $COOR^8$ (IVa), reducing this by means of a reducing agent to give an intermediate of the formula (IV) in which X' is $CH_2OH$ (IVb), and C. reacting the resulting intermediate of the formula (IVb) according to one of the following reactions:

a) selective oxidation to form a compound of the formula (I) where X=CHO or b) replacement of the OH group by a halogen or pseudohalogen by means of nucleophilic substitution to form a compound of the formula (I) where Z=Cl, Br, I, CN, SCN, OCN; and D. if desired, converting compounds of the formula (I) where Z=Cl, Br, I into a biaryl derivative of the formula (I) where Z=$PO(OR^1)_2$, $PO(R^2)_2$, $P(R^3)_3^+$ $A^-$ by reaction with the corresponding organophosphorus compounds.

A significant advantage of the process of the present invention is that the biaryl derivatives can generally be purified in a simple manner, in particular by recrystallization.

Although most compounds of the formula (IV) where X'=COOR and of the formula (I) where X=$CH_2Cl$, $CH_2Br$ are high-boiling oils, they can generally be obtained in pure form from the synthesis. The coupling reactions selected according to the invention can routinely be carried out such that the resulting products (IV) are obtained in purities of greater than 90%. The reaction to form bishalides of the formula (I) generally leads only to low by-product formation, so that these substances are obtained in a purity similar to that of the bisalcohols (IV) used. These in turn are generally crystalline substances which can readily be purified to purities of greater than 99% by simple recrystallization. The same applies to the bisphosphonates and, in particular, bisphosphonium salts of the formula (I). In the case of the bisaldehydes of the formula (I), a highly viscous oil or a crystalline substance is obtained depending on the substitution pattern. If the reaction conditions in the preparation are chosen according to the invention (e.g. Swern oxidation), the bisaldehyde is likewise obtained in high purity directly from the reaction mixture.

The process of the invention is depicted in Scheme 1.

Scheme 1

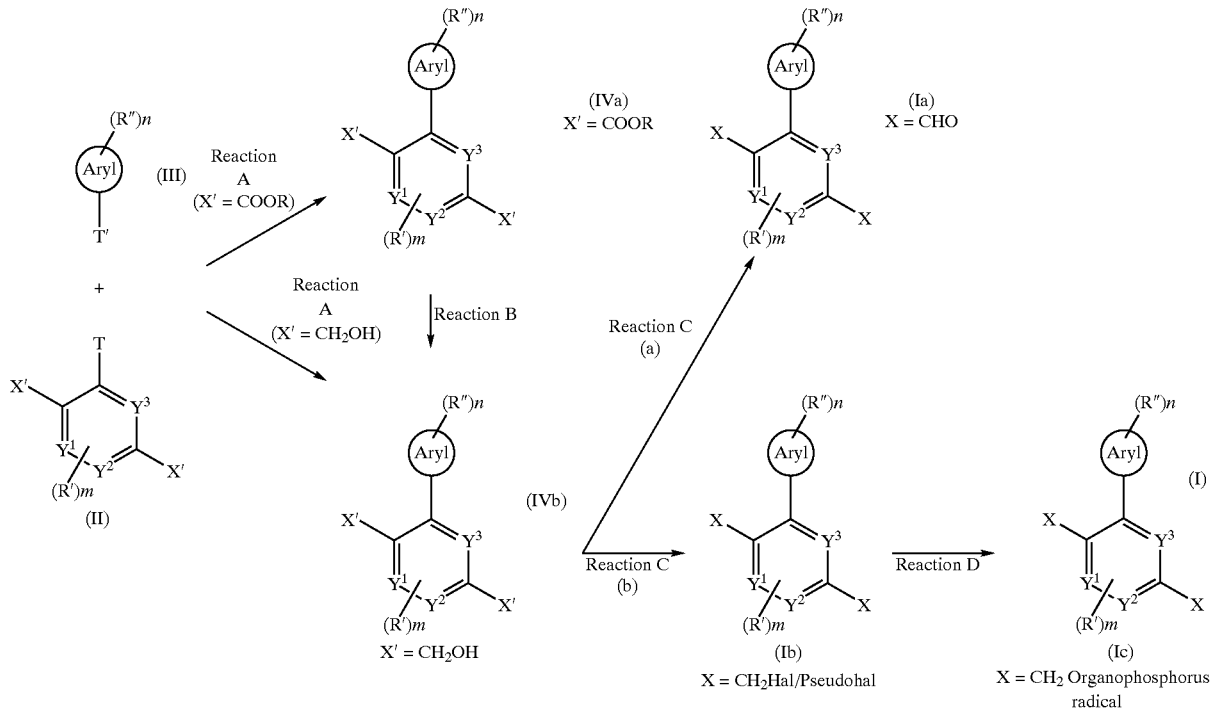

The starting compounds of the formulae (II) and (III) are very readily obtainable, since some of them are commercially available, e.g. bromoterephthalic acid, or they can be prepared in a simple manner and in large amounts from commercially available compounds.

Scheme 2
Preparation of the starting compound (II)

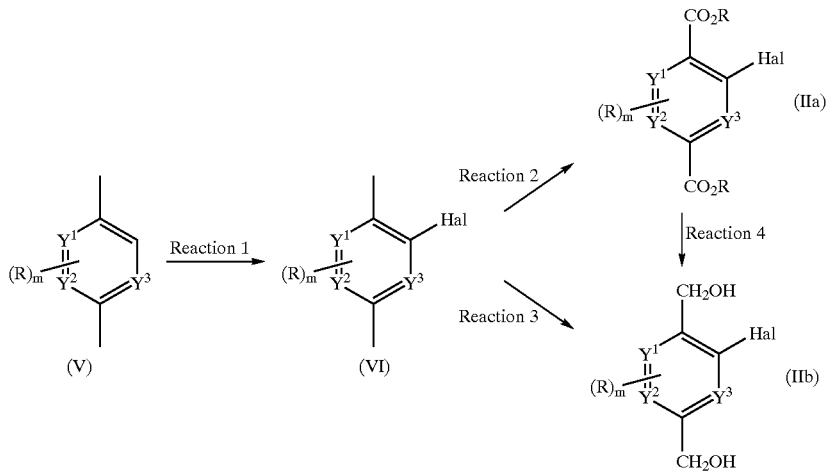

The following may be said about the reactions in Scheme 2: the 1,4-dimethyl compound (V) is generally commercially available (e.g. p-xylene, 2,5-dimethylphenol, 2,5-dimethylaniline, 2,5-dimethylbenzonitrile, 2,5-dimethylpyridine) or is simple to prepare from commercially available compounds (e.g. alkylation of a corresponding phenol or amine), compound (V) can be halogenated, e.g. chlorinated or brominated, on the aromatic by standard methods (see, for example, Organikum, VEB Deutscher Verlag der Wissenschaften, 15th edition, p. 391 ff., Leipzig 1984). The resulting compounds (VI) are obtainable in good yields and in industrial amounts; the compound (VI) is sometimes also commercially available (e.g. 2-bromo-p-xylene).

(VI) can be reacted, preferably catalytically (cobalt catalyst, atmospheric oxygen, see, for example, EP-A 0 121 684) to give the corresponding 1,4-dicarboxylic acids (IIa). If the reaction conditions are chosen appropriately, this is routinely possible regardless of the substituent. The resulting acids, (IIa) with R=H, can be converted, if desired, into corresponding esters (R≠H) by standard methods.

The compounds of the formula (IIa), which are obtained virtually quantitatively in this way, can be converted into the bisalcohols (IIb) by means of well-known reduction reactions. The bisalcohols are also obtainable directly from the compounds of the formula (VI) by oxidation (see, for example, A. Belli et al., Synthesis 1980, 477).

If desired, the halogen atom can be replaced at an appropriate stage, as described below for the compounds of the formula (IIIa), by a boronic acid (ester) or trialkyltin group.

The corresponding perfluoroalkylsulfonates can be prepared, for example, by esterification of corresponding phenol functions.

Scheme 3
Preparation of the starting compound (III)

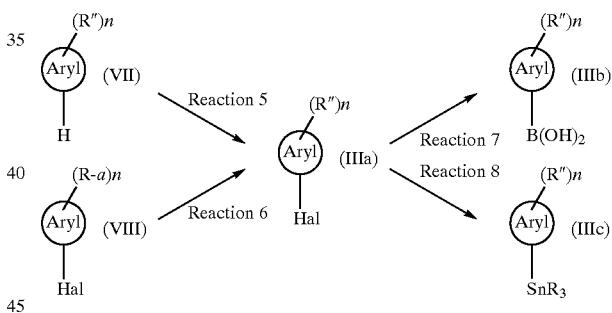

The following may be said about Scheme 3: The compounds (VII) are generally commercially available (e.g. various alkylaromatics and dialkylaromatics, alkoxyaromatics) or are simple to prepare from appropriate precursors (e.g. hydroquinone, catechol, naphthol), e.g. by alkylation. Compound (VII) can then be converted as described above into compounds of the formula (IIIa) by simple halogenation reactions (reaction 5). Many compounds of the formula (VIII) are inexpensive chemicals (e.g. bromophenol, bromoaniline) which are simple to convert into compounds of the formula (IIIa) by means of Reaction 6 (e.g. alkylation of phenol functions). The compounds of the formula (IIIa) are then metallated by means of appropriate reagents (e.g. Mg turnings, n-BuLi, s-BuLi) and can then be converted by appropriate further reaction, e.g. with trialkyltin chloride, trialkyl borate, into the corresponding compounds of the formula (IIIb) or (IIIc).

It has thus been shown that the starting compounds (II) and (III) are obtainable in a simple way and in the variety required.

According to the invention, the starting compounds (II) and (III) are converted into intermediates of the formula (IV) by means of a coupling reaction (Reaction A in Scheme 1).

For this purpose, the compounds of the formulae (II) and (III) are reacted in an inert solvent at a temperature in the range from 0° C. to 200° C. in the presence of a palladium catalyst.

Here, one of the compounds, preferably that of the formula (II), contains a halogen or perfluoroalkylsulfonate group while the other contains a boronic acid (ester) group (IIIb) or a trialkyltin group (IIIc).

To carry out the reaction A according to the invention using boronic acid (ester)s in the formula (IIIb), variant Aa, Suzuki coupling, the aromatic boron compound, the aromatic halogen compound or the perfluoroalkylsulfonate, a base and catalytic amounts of the palladium catalyst are added to water or to one or more inert organic solvents or preferably to a mixture of water and one or more inert organic solvents and reacted, e.g. stirred, at a temperature of from 0° C. to 200° C., preferably from 30° C. to 170° C., particularly preferably from 50° C. to 150° C., very particularly preferably from 60° C. to 120° C., for a period of from 1 hour to 100 hours, preferably from 5 hours to 70 hours, particularly preferably from 5 hours to 50 hours. The crude product can be purified by methods known to those skilled in the art and matched to the particular product, e.g. by recrystallization, distillation, sublimation, zone melting, melt crystallization or chromatography.

Organic solvents suitable for the process of the invention are, for example, ethers such as diethyl ether, dimethoxymethane, diethylene glycol dimethyl ether, tetrahydrofuran, dioxane, dioxolane, diisopropyl ether and tert-butyl methyl ether, hydrocarbons such as hexane, isohexane, heptane, cyclohexane, toluene and xylene, alcohols such as methanol, ethanol, 1-propanol, 2-propanol, ethylene glycol, 1-butanol, 2-butanol and tert-butanol, ketones such as acetone, ethyl methyl ketone, isobutyl methyl ketone, amides such as dimethylformamide, dimethylacetamide and N-methylpyrrolidone, nitriles such as acetonitrile, propionitrile and butyronitrile, and mixtures thereof.

Preferred organic solvents are ethers such as dimethoxyethane, diethylene glycol dimethyl ether, tetrahydrofuran, dioxane and diisopropyl ether, hydrocarbons such as hexane, heptane, cyclohexane, toluene and xylene, alcohols such as methanol, ethanol, 1-propanol, 2-propanol, 1-butanol, 2-butanol, tert-butanol and ethylene glycol, ketones such as ethyl methyl ketone and isobutyl methyl ketone, amides such as dimethylformamide, dimethylacetamide and N-methylpyrrolidone, and mixtures thereof.

Particularly preferred solvents are ethers such as dimethoxyethane and tetrahydrofuran, hydrocarbons such as cyclohexane, toluene and xylene, alcohols such as ethanol, 1-propanol, 2-propanol, 1-butanol and tert-butanol, and mixtures thereof.

In a particularly preferred variant, use is made of water and one or more water-insoluble solvents.

Examples are mixtures of water and toluene and of water, toluene and tetrahydrofuran.

Bases which are preferably used in the process of the invention are alkali metal and alkaline earth metal hydroxides, alkali metal and alkaline earth metal carbonates, alkali metal hydrogen carbonates, alkali metal and alkaline earth metal acetates, alkali metal and alkaline earth metal alkoxides and also primary, secondary and tertiary amines.

Particular preference is given to alkali metal and alkaline earth metal hydroxides, alkali metal and alkaline earth metal carbonates and alkali metal hydrogen carbonates.

Very particular preference is given to alkali metal hydroxides such as sodium hydroxide and potassium hydroxide, and also alkali metal carbonates and alkali metal hydrogen carbonates, e.g. lithium carbonate, sodium carbonate and potassium carbonate.

The base is preferably used in an amount of from 100 to 1000 mol %, particularly preferably from 100 to 500 mol %, very particularly preferably from 150 to 400 mol %, in particular from 180 to 250 mol %, based on the aromatic boron compound.

The palladium catalyst comprises palladium metal or a palladium(0) or (II) compound and a complexing ligand, preferably a phosphine ligand.

The two components can form a compound, e.g. the particularly preferred $Pd(PPh_3)_4$, or be used separately.

Suitable palladium components are, for example, palladium compounds such as palladium ketonates, palladium acetylacetonates, nitrilepalladium halides, olefinpalladium halides, palladium halides, allylpalladium halides and palladium biscarboxylates, preferably palladium ketonates, palladium acetylacetonates, bis-$\eta^2$-olefinpalladium dihalides, palladium(II) halides, $\eta^3$-allylpalladium halide dimers and palladium biscarboxylates, very particularly preferably bis (dibenzylideneacetone)palladium(0) [$Pd(dba)_2$], $Pd(dba)_2$) .$CHCl_3$, palladium bisacetylacetonate, bis(benzonitrile) palladium dichloride, $PdCl_2$, $Na_2PdCl_4$, dichlorobis (dimethyl sulfoxide)palladium(II), bis(acetonitrile) palladium dichloride, palladium(II) acetate, palladium(II) propionate, palladium(II) butanoate and (1c,5c-cyclooctadiene)palladium dichloride.

A further suitable catalyst is palladium in metallic form, hereinafter referred to simply as palladium, preferably palladium in powder form or on a support material, e.g. palladium on activated carbon, palladium on aluminum oxide, palladium on barium carbonate, palladium on barium sulfate, palladium on aluminum silicates such as montmorillonite, palladium on $SiO_2$ and palladium on calcium carbonate, in each case having a palladium content of from 0.5 to 10% by weight. Particular preference is given to palladium in powder form, palladium on activated carbon, palladium on barium carbonate and/or calcium carbonate and palladium on barium sulfate, in each case having a palladium content of from 0.5 to 10% by weight. Very particular preference is given to palladium on activated carbon having a palladium content of 5 or 10% by weight.

In the process of the invention, the palladium catalyst is used in an amount of from 0.1 to 10 mol %, preferably from 0.05 to 5 mol %, particularly preferably from 0.1 to 3 mol %, very particularly preferably from 0.1 to 1.5 mol %, based on the aromatic halogen compound or the perfluoroalkylsulfonate.

Complexing ligands suitable for the process of the invention are, for example, phosphines such as trialkylphosphines, tricycloalkylphosphines and triarylphosphines, where the three substituents on the phosphorus can be identical or different, chiral or achiral and one or more of the ligands can link the phosphorus groups of a plurality of phosphines and part of this linkage can also be one or more metal atoms. Examples of phosphines which can be used in the process of the present invention are trimethylphosphine, tributylphosphine, tricyclohexylphosphine, triphenylphosphine, tritolylphosphine, tris(4-dimethylaminophenyl)phosphine, bis(diphenylphosphino)methane, 1,2-bis (diphenylphosphino) ethane, 1,3-bis(diphenylphosphino) propane and 1,1'-bis(diphenylphosphino)ferrocene. Further suitable ligands are, for example, diketones such as acetylacetone and octafluoroacetylacetone and tertiary amines such as trimethylamine, triethylamine, tri-n-propylamine and triisopropylamine.

Preferred complexing ligands are phosphines and diketones, particularly preferably phosphines.

Very particularly preferred complexing ligands are triphenylphosphine, 1,2-bis(diphenylphosphino)ethane, 1,3-bis(diphenylphosphino)propane and 1,1'-bis(diphenylphosphino)ferrocene, in particular triphenylphosphine.

Further complexing ligands suitable for the process of the invention are water-soluble complexing ligands which contain, for example, sulfonic acid salt groups and/or sulfonic acid groups and/or carboxylic acid salt groups and/or carboxylic acid groups and/or phosphonic acid salt groups and/or phosphonic acid groups and/or phosphonium groups and/or peralkylammonium groups and/or hydroxy groups and/or polyether groups of suitable chain length.

Preferred classes of water-soluble complexing ligands are phosphines such as trialkylphosphines, tricycloalkylphosphines, triarylphosphines, dialkylarylphosphines, alkyldiarylphosphines and heteroarylphosphines such as tripyridylphosphine and trifurylphosphine, where the three substituents on the phosphorus can be identical or different, chiral or achiral and one or more of the ligands can link the phosphorus groups of a plurality of phosphines and part of this linkage can also be one or more metal atoms, phosphites, phosphinous esters and phosphonic esters, phospholes, dibenzophospholes and phosphorus-containing cyclic, oligocyclic and polycyclic compounds in each case substituted by the abovementioned groups.

The complexing ligand is generally used in an amount of from 0.1 to 20 mol %, preferably from 0.2 to 15 mol %, particularly preferably from 0.5 to 10 mol %, very particularly preferably from 1 to 6 mol %, based on the aromatic halogen compound or the perfluoroalkylsulfonate.

It is also possible to use mixtures of two or more different complexing ligands.

All or part of the boronic acid derivative used according to the invention can be present as anhydride.

Advantageous embodiments of parts of the process of the invention in variant Aa are described, for example, in WO-A-94/101 05, EP-A-679 619, EP-A 694 530 and PCT/EP 96/03154, which are hereby expressly incorporated by reference into the description of the present application.

In the variant Ab, also known as Stille coupling, an aromatic tin compound, preferably of the formula (IIIc), is reacted with an aromatic halogen compound or an aromatic perfluoroalkylsulfonate, preferably of the formula (II), at a temperature in the range from 0° C. to 200° C. in an inert organic solvent in the presence of a palladium catalyst.

An overview of this reaction may be found, for example, in J. K. Stille, Angew. Chemie Int. Ed. Engl. 1986, 25, 508.

To carry out the process, the aromatic tin compound and the aromatic halogen compound or the perfluoroalkylsulfonate are preferably added to one or more inert organic solvents and reacted, e.g. stirred, at a temperature of from 0° C. to 200° C., preferably from 30° C. to 170° C., particularly preferably from 50° C. to 150° C., very particularly preferably from 60° C. to 120° C., for a period of from 1 hour to 100 hours, preferably from 5 hours to 70 hours, particularly preferably from 5 hours to 50 hours. After the reaction is complete, the Pd catalyst obtained as a solid is separated off, for example by filtration, and the crude product is freed of the solvent or solvents. The product can be further purified by methods known to those skilled in the art and matched to the particular product, e.g. by recrystallization, distillation, sublimation, zone melting, melt crystallization or chromatography.

Suitable organic solvents are, for example, ethers such as diethyl ether, dimethoxymethane, diethylene glycol dimethyl ether, tetrahydrofuran, dioxane, dioxolane, diisopropyl ether and tert-butyl methyl ether, hydrocarbons such as hexane, isohexane, heptane, cyclohexane, benzene, toluene and xylene, alcohols such as methanol, ethanol, 1-propanol, 2-propanol, ethylene glycol, 1-butanol, 2-butanol and tert-butanol, ketones such as acetone, ethyl methyl ketone and isobutyl methyl ketone, amides such as dimethylformamide (DMF), dimethylacetamide and N-methylpyrrolidone, nitriles such as acetonitrile, propionitrile and butyronitrile, and mixtures thereof.

Preferred organic solvents are ethers such as dimethoxyethane, diethylene glycol dimethyl ether, tetrahydrofuran, dioxane and diisopropyl ether, hydrocarbons such as hexane, heptane, cyclohexane, benzene, toluene and xylene, alcohols such as methanol, ethanol, 1-propanol, 2-propanol 1-butanol, 2-butanol, tert-butanol and ethylene glycol, ketones such as ethyl methyl ketone and amides such as DMF.

Particularly preferred solvents are amides; very particular preference is given to DMF.

The palladium catalyst comprises palladium metal or a palladium(0) or (II) compound and a complexing ligand, preferably a phosphine ligand.

The two components can form a compound, e.g. $Pd(PPh_3)_4$, or be used separately.

Suitable palladium components are, for example, palladium compounds such as palladium ketonates, palladium acetylacetonates, nitrilepalladium halides, olefinpalladium halides, palladium halides, allylpalladium halides and palladium biscarboxylates, preferably palladium ketonates, palladium acetylacetonates, bis-$\eta^2$-olefinpalladium dihalides, palladium(II) halides, $\eta^3$-allylpalladium halide dimers and palladium biscarboxylates, very particularly preferably bis(dibenzylideneacetone)palladium(0) [$Pd(dba)_2$], $Pd(dba)_2$·$CHCl_3$, palladium bisacetylacetonate, bis(benzonitrile)palladium dichloride, $PdCl_2$, $Na_2PdCl_4$, dichlorobis(dimethyl sulfoxide)palladium(II), bis(acetonitrile)palladium dichloride, palladium(II) acetate, palladium(II) propionate, palladium(II) butanoate and (1c,5c-cyclooctadiene)palladium dichloride.

In this variant of the process of the invention, the palladium catalyst is generally used in an amount of from 0.01 to 10 mol %, preferably from 0.05 to 5 mol %, particularly preferably from 0.1 to 3 mol %, very particularly preferably from 0.1 to 1.5 mol %, based on the aromatic halogen compound or the perfluoroalkylsulfonate.

Suitable ligands are, for example, phosphines such as trialkylphosphines, tricycloalkylphosphines and triarylphosphines, where the three substituents on the phosphorus can be identical or different, chiral or achiral and one or more of the ligands can link the phosphorus groups of a plurality of phosphines and part of this linkage can also be one or more metal atoms.

In this variant of the process of the invention, the ligand is generally used in an amount of from 0.1 to 20 mol %, preferably from 0.2 to 15 mol %, particularly preferably from 0.5 to 10 mol %, very particularly preferably from 1 to 6 mol %, based on the aromatic halogen compound or the perfluoroalkylsulfonate.

Reaction B

If the group X' in the intermediate (IV) is —COOR, the intermediate is reduced to the bisalcohol, X'=$CH_2OH$.

The reduction can be carried out by known methods with which those skilled in the art are familiar, as are described, for example, in Houben-Weyl, 4th edition, vol. 6, 16, chapter VIII, Georg-Thieme-Verlag, Stuttgart 1984.

Preferred embodiments are
a) reaction with Li—AlH$_4$ or diisobutylaluminum hydride (DIBAL-H) in tetrahydrofuran (THF) or toluene, as described, for example, in Organikum (see above), p. 612 ff.;
b) reaction with boron hydrides such as BH$_3$, as described, for example, in Houben-Weyl, 4th edition, vol. 6, 16, chapter VIII, pp. 211–219, Georg-Thieme-Verlag, Stuttgart 1984;
c) reaction with hydrogen in the presence of a catalyst, as described, for example, in Houben-Weyl, 4th edition, vol. 6, 16, chapter VIII, p. 110 ff., Georg-Thieme-Verlag, Stuttgart 1984, and
d) reaction with sodium or sodium hydride.

Particular preference is given to the reduction using LiAlH$_4$ or DIBAL-H.

Reaction C a

The bisalcohols of the formula (IV) (X=CH$_2$OH) obtained from the reaction A or B can be converted into bisaldehydes of the formula (I) by selective oxidation.

Such an oxidation can be carried out by methods known per se with which those skilled in the art are familiar, as are described, for example, in R. C. Laroch, Comprehensive Organic Transformations, VCH, 1989, pp. 604–614, and the literature cited therein.

Preference is given to:
a) oxidation using dimethyl sulfoxide/oxalyl chloride (Swern oxidation), as is described, for example, in A. J. Mancoso, D. Swern, Synthesis 1981, 165, and
b) oxidation using pyridinium chlorochromate (PCC) or pyridinium dichromate, as is described, for example, in Houben-Weyl, 4th edition, volume E3, pp. 291–296, Georg-Thieme Verlag, Stuttgart, 1983.

The resulting aldehydes can be used for polymerization reactions, e.g. by the Wittig/Horner or Knoevenagel method.

Reaction C b

According to the invention, the OH groups in the bisalcohols of the formula (IV) can be replaced by halogen or pseudohalogen by means of nucleophilic substitution.

To prepare chlorides and bromides, preference is given to reacting the corresponding bisalcohol with HCl or HBr, for example in glacial acetic acid (see, for example, Houben-Weyl, volume 5/4, p. 385 ff, 1960) or with thionyl chloride or bromide, in the presence or absence of a catalyst (see, for example, Houben-Weyl, volume 5/1 b,p. 862 ff., 1962).

Chlorides can also be prepared by reaction with phosgene (see, for example, Houben-Weyl, volume V, 3, p. 952 ff., 1962), and bromides by reaction with PBr$_3$.

Iodides are preferably prepared by reaction with phosphorus/iodine by the method of A. I. Vogel (see, for example, Houben-Weyl, volume V, 4, p. 615ff., 1969).

The work-up is in all cases carried out in a simple manner by known methods with which those skilled in the art are familiar. The resulting compounds of the formula (I) can, be advantageously used for polymerization reactions, for example dehydrohalogenations or Knoevenagel condensations (Z=CN).

Reaction D

The halogen compounds of the formula (Ib) can be readily converted into bis(diphenylphosphine oxides) or bis(phosphonic esters) of the formula (Ic) by, for example, the Michaelis-Arbusov reaction of the appropriate bis(halomethyl) compounds with ethyl diphenylphosphinite (C$_6$H$_5$)P—O—C$_2$H$_5$ or triethyl phosphite.

Bisphosphonium salts can likewise be obtained in a simple way by reacting the halides with, for example, triarylphosphines.

The compounds obtained in this way can be used for Wittig/Horner polymerization reactions.

Products of the process of the invention are polymerizable biaryls of the formula (I),

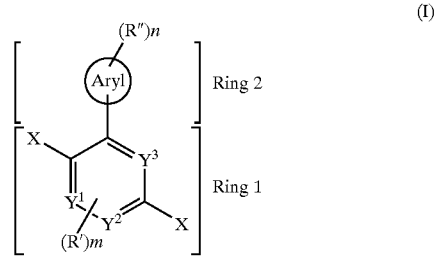

where the symbols and indices are as defined above.

Preference is given to compounds of the formula (I) in which the symbols and indices have the following meanings:

X: —CH$_2$Z, CHO;

Z: Cl, Br, CN, PO(OR$^1$)$_2$, PO(R$^2$)$_2$, P(R$^3$)$_3{}^\oplus$A$^\ominus$;

Y$^1$, Y$^2$, Y$^3$: CH;

Aryl: phenyl, 1- or 2-naphthyl, 1-, 2- or 9-anthracenyl, 2-, 3- or 4-pyridinyl, 2-, 4- or 5-pyrimidinyl, 2-pyrazinyl, 3- or 4-pyridazinyl, 2-, 3-, 4-, 5-, 6-, 7- or 8-quinolyl, 2- or 3-thiophenyl, 2- or 3-pyrrolyl, 2- or 3-furanyl or 2-(1,3,4-oxadiazol)yl;

R': identical or different, straight-chain or branched alkoxy group having from 1 to 12 carbon atoms;

R": identical or different, straight-chain or branched alkyl or alkoxy group having from 1 to 12 carbon atoms;

m: 0, 1, particularly preferably 0;

n: 1, 2, 3, particularly preferably 1, 2.

Particular preference is given to compounds in which ring 2 is phenyl, 1-naphthyl, 2-naphthyl or 9-anthracenyl.

Furthermore, the following substitution patterns are preferred in ring 2:

2-, 3- or 4-alkyl(oxy)phenyl, 2,3-, 2,4-, 2,5-, 2,6-, 3,4- or 3,5-dialkyl(oxy)phenyl, 2,3,4-, 2,3,5-, 2,3,6-, 2,4,5-, 2,4,6- or 3,4,5-trialkyl(oxy)phenyl, 2-, 3-, 4-, 5-, 6-, 7- or 8-alkyl(oxy)-1-naphthyl, 1-, 3-, 4-, 5-, 6-, 7- or 8-alkyl(oxy)-2-naphthyl and 10-alkyl(oxy)-9-anthracenyl.

Preferred starting compounds of the formulae (II) and (III) are unambiguously given by the preference for the end products.

The polymerizable biaryls of the formula (I) are new and are suitable as intermediates for preparing new polymers having a particular suitability as electroluminescence materials.

They are likewise subject matter of the invention.

The invention also provides for the use of polymerizable biaryls of the formula (I) for preparing polymers which are preferably used as electroluminescence materials.

In the present application, various documents have been cited, for example to illustrate the background to the invention. All of these documents are hereby expressly incorporated by reference into the present application. The contents of the German Patent Application 196 51 439.8, whose priority is claimed by the present application, and also the abstract of the present application are hereby expressly incorporated by reference into the present application.

BRIEF DESCRIPTION OF THE DRAWINGS

FIGS. I–III demonstrate the priority of the compounds by NMR.

The invention is illustrated by the examples, without being restricted thereby.

A. Synthesis of Compounds of the Formula (II)

EXAMPLE A1

Synthesis of Diethyl 2-Bromoterephthalate and 2-Bromo-1,4-bis(hydroxymethyl)benzene a) Synthesis of 2-Bromo-p-xylene:

p-Xylene (934.4 g; 8.8 mol) and Fe powder (16 g) were placed in a reaction vessel and about 20 ml of bromine were slowly added dropwise. The commencement of the reaction (after about 10 minutes) could be observed by means of the evolution of gas. After the reaction had started, the remaining bromine (total: 1278.4 g; 8.0 mol) was added dropwise at RT, with water bath cooling (4 hours). The mixture was stirred for another 2 hours at RT. The slightly brownish reaction solution was filtered and stirred first with water, then with 480 ml of saturated aqueous $Na_2SO_3$ solution, subsequently shaken once more with dilute aqueous NaOH and twice with $H_2O$; the organic phase (clear and colorless) was dried with $MgSO_4$, filtered and purified by being distilled twice under reduced pressure (diaphragm pump/oil bath, about 100–120° C./60 cm column).

Product (b.p. about 85–89° C. at 13-9 mbar; oil bath=120–155° C.): 1234.1 g (83.4%); $^1$H NMR (400 MHz; $CDCl_3$); δ [ppm]=7.33 (dd; 1H; $J_1$=2, $J_2$=0.7 Hz; H-3), 7.06 (d (br); 1H; $J_1$=8 Hz; H-6), 6.97 (dd; 1H; $J_1$=8, $J_2$=2 Hz; H-5), 2.33 and 2.26 (each: s (br); 3H; Me).

b) Synthesis of 2-Bromoterephthalic Acid:

A 1 l Hastelloy C22 autoclave was charged with a solution of bromo-p-xylene (92.5 g, 0.5 mol), cobalt acetate tetrahydrate (0.62 g, 2.5 mmol), manganese acetate tetrahydrate (0.61 g, 2.5 mmol), hydrogen bromide (0.4 g, 5.0 mmol) and potassium acetate (0.98 g, 10 mmol) in 350 g of glacial acetic acid.

The solution was heated in a nitrogen atmosphere (18 bar) while stirring. At 154° C., compressed air was passed through the solution (18 bar; air input about 180 liters per hour). The reaction commenced immediately. The reaction temperature was held at about 165° C. by means of external cooling. After 1 hour, the exothermic reaction is complete, the reactor contents were again blanked with nitrogen and cooled to 100° C. The suspension taken out at this temperature was cooled to 20° C. while stirring and the crystals were filtered off.

After washing three times with 50 ml each time of glacial acetic acid, the colorless product was dried at 50° C. and 65 mbar. Product: colorless, microcrystalline powder, 102.2 g (83.7% of theory), melting point=302° C.

$^1$H NMR (400 MHz; $d_6$-DMSO): δ [ppm]=13.7 (br; 2H; $CO_2H$), 8.18 (d; 1H; $J_1$=2 Hz; H-3), 8.02 (dd; 1H; $J_1$=8, $J_2$=2 Hz; H-5), 7.85 (d; 1H; $J_1$=8 Hz; H-6).

c1) First Synthetic Route to Diethyl 2-Bromoterephthalate:

2-bromoterephthalic acid (122.52 g; 0.5 mol) was suspended in ethanol (138 g; 3 mol) and carbon tetrachloride (150 ml), 15 ml of sulfuric acid were added by means of a pipette and the mixture was refluxed for 5 days while stirring vigorously. The suspension changed into a clear solution within about 24 hours, but the reaction was complete only after 5 days (monitoring by TLC). Subsequently, the phases were separated and the organic phase was shaken with $H_2O$ and with aqueous $NaHCO_3$ solution, with the upper aqueous phase becoming slightly alkaline. After shaking once more with $H_2O$, the organic phase was dried over $Na_2SO_4$ and the solvent was taken off. The desired product was obtained almost pure (97–98%) without further purification as a yellowish, slightly viscous oil: 118 g (78%), d=1.38 kg/dm$^3$. Fractional vacuum distillation was suitable for further purification. 99.9% pure product ($^1$H NMR) was obtained at 1.1 mbar and 142° C.

$^1$H NMR (400 MHz; $CDCl_3$); δ [ppm]=8.30 (d; 1H; $J_1$=1.7 Hz; H-3), 8.01 (dd; 1H; $J_1$=8, $J_2$=1.7 Hz; H-5), 7.79 (d; 1H; $J_1$=8 Hz; H-6), 4.43, 4.41 (each: q; 2H; J=7.1 Hz; O—$CH_2$), 1.42, 1.41 (each: t; 3H; J=7.1 Hz; $CH_3$).

c2) Second Synthetic Route to Diethyl 2-Bromoterephthalate:

Bromoterephthalic acid (500 g; 2.04 mol) was placed under protective gas in a reaction vessel, mixed at room temperature with $SOCl_2$ (728 g, 446 ml, 6.12 mol) while stirring and 3 drops of DMF (N,N-dimethylformamide) were added. Even after the end of the 90 minute addition, the mixture was a thick slurry and therefore difficult to stir. It was subsequently heated to an internal temperature of 60° C. and stirred for 4 days at this temperature; this resulted in a clear solution. The mixture was freed of excess thionyl chloride by adding 2×100 ml of toluene and the thionyl chloride/toluene mixture was in each case distilled off at atmospheric pressure (bath temperature=140°). The resulting liquid acid chloride was admixed with absolute ethanol (460 g, 583 ml, 10 mol) over a period of about 50 minutes while cooling on a water bath (temperature rise to 45°) and refluxed overnight. Impurities were filtered off and the solvent was taken off. The honey-colored, slightly viscous product was dried in an oil pump vacuum: 612.7 g (+99% of theory); about 97% pure ($^1$H NMR).

NMR: analogous to c1). Further purification analogous to c1.

c3) Third Synthetic Route to Diethyl 2-Bromoterephthalate:

Bromoterephthalic acid (49 g, 0.2 mol) and EtOH (184 g, 233 ml, 4.0 mol) were placed under protective gas in a reaction vessel and then treated with $H_2SO_4$ (1 ml) at RT while stirring. The mixture was subsequently refluxed (78° C.). The initially white suspension had become a clear solution after 20 minutes. The ethanol was distilled off until the internal temperature had reached 110° C. Subsequently, more fresh ethanol (200 ml) was added and the procedure was repeated from the beginning. This procedure was repeated a total of five times, after which the reaction was complete according to TLC. At the end of the reaction, remaining ethanol was distilled off as completely as possible, the reaction mixture was admixed with a little ethyl acetate and shaken first with aqueous $NaHCO_3$ solution and finally with $H_2O$ until neutral. The organic solvent was taken off and the oily product was dried under an oil pump vacuum: 56.6 g (94%), purity (according to $^1$H-NMR) about 97%. Further purification analogous to c1.

NMR: analogous to c1).

d) Synthesis of 2-Bromo-1,4-bishydroxymethylbenzene:

1st step:

122.82 g (0.50 mol) of bromoterephthalic acid were placed in a reaction vessel and, under $N_2$, 3 drops of DMF were added. 110 ml (1.5 mol) of $SOCl_2$ were added dropwise at room temperature, first slowly and then quickly (suspension somewhat more stirrable, but still a thick slurry; time: about 70 minutes). The suspension was carefully heated and stirred for 7 hours at an internal temperature of 55° C. After standing overnight at room temperature, the mixture was freed of excess thionyl chloride by distillation. For this purpose, the mixture was admixed with 2×50 ml of hexane and the thionyl chloride/hexane mixture was each time distilled off at atmospheric pressure. Finally, a vacuum of 100 mbar was applied for about 30 minutes.

2nd step:

23.1 g (0.6 mol) of $LiAlH_4$ were admixed with 500 Ml of absolute THF under $N_2$. A solution from the 1st step (about 90 ml) in 200 ml of absolute THF was added dropwise to the gray suspension at room temperature (time: about 3 hours). The mixture was then heated to reflux and stirred for 5.5 hours. After cooling to room temperature, the beige suspension was cooled further on an ice bath. 46 g of ice water were carefully added dropwise (time: about 1 hour). After a further 50 ml of $H_2O$ had been added, 100 ml of 1 N aqueous $H_2SO_4$ and then 90 ml of ½-concentrated aqueous $H_2SO_4$ were added dropwise. 2 phases were obtained: upper: yellow, homogeneous; lower: gray suspension. The phases were separated and the lower, gray phase was extracted twice with 200 ml each time of ethyl acetate. The combined organic phases were extracted 4 times with 200 ml each time of $H_2O$ and finally evaporated to dryness. This gave the crude product as a beige solid (110 g) which could be further purified by recrystallization ($H_2O$/ethanol 2/1). Product: colorless needles (78 g; 72%), melting point: 106–108° C.

$^1H$ NMR (400 MHz; $d_6$-acetone): δ [ppm]=7.55 (m; 2H; H-3, H-6), 7.35 (dd; 1H; $J_1$=8, $J_2$=1.9 Hz; H-5), 4.66, 4.62 (each: d; 2H; J=5.9 Hz; $CH_2$—O), 4.37, 4.28 (each: t; 1H; J=5.9 Hz; OH).

EXAMPLE A2

Synthesis of Diethyl 2-Bromo-5-methoxyterephthalate a) Synthesis of 4-Bromo-2,5-dimethylanisole Bromine (291.5 g, 1835 mmol) was added dropwise to a mixture of 2,5-dimethylanisole (250 g, 1835 mmol) and Fe powder (3.25 g) while stirring. The commencement of the reaction could be observed by means of the evolution of gas. The remaining bromine was then added dropwise over a period of 30–40 minutes at room temperature while cooling on a water bath. The reaction mixture was stirred further for about 4 hours. The solution was subsequently separated from the Fe powder, a little chloroform was added and the mixture was shaken with water, leading to the solution becoming lighter in color. After shaking with 50 ml of saturated aqueous $Na_2SO_3$ solution, the solution had become completely decolorized. It was shaken once more with dilute aqueous NaOH and twice with $H_2O$ and, after drying, the solvent was taken off. The crude product was fractionally distilled under reduced pressure.

The product was obtained as a viscous, colorless oil (boiling point=68° C., 0.8 mbar): 285 g (72%).

$^1H$ NMR ($CDCl_3$); δ [ppm]=7.25 (s; 1H, H-aryl), 6.68 (s, 1H, H-aryl), 3.78 (s, 3H, O—Me), 2.36, 2.14 (each s, 3+3H, $CH_3$).

b) Synthesis of 2-Bromo-5-methoxyterephthalic Acid

A 1 l autoclave (HC-22) fitted with disk stirrer, reflux condenser, gas inlet and gas outlet was charged with a solution of cobalt acetate tetrahydrate (1.25 g, 5 mmol), manganese acetate tetrahydrate (1.23 g), HBr (0.81 g), sodium acetate (1.37 g) and 4-bromo-2,5-dimethylanisole (107.5 g, 0.5 mol) in 380 g of glacial acetic acid. The reaction solution was heated under a nitrogen atmosphere (17 bar) to 150° C. while stirring. At this temperature, air (17 bar) was passed through the solution (180–200 l/h), whereupon the exothermic reaction started immediately. The reaction temperature was maintained at 150° C. by external cooling. After about 45 minutes, the exothermic reaction was complete. To make an after-reaction possible, an air/nitrogen mixture (10% of $O_2$) was passed through for 30 minutes at 150° C. The introduction of air was then stopped and nitrogen was introduced.

The reactor contents were cooled to 100° C. under a nitrogen atmosphere, drained as solution into a flask and cooled to 20° C. while stirring. This resulted in the product crystallizing out. The colorless crystal slurry was filtered with suction and the crystals were washed four times with 40 g each time of glacial acetic acid.

Drying gave 96.2 g of 2-bromo-5methoxyterephthalic acid (70%).

$^1H$ NMR (DMSO); δ [ppm]=13.5 (br, 2H, COOH), 7.87 (s, 1H, H-aryl), 7.42 (s, 1H, H-aryl), 3.88 (s, 3H, O—Me).

c) Synthesis of Diethyl 2-Bromo-5-methoxyterephthalate 2-bromo-5-methoxyterephthalic acid (202.89 g, 738 mmol) together with 500 ml of EtOH were placed under protective gas in a reaction vessel and $H_2SO_4$ was then added while stirring at RT. The mixture was subsequently refluxed at an internal temperature of 78° C. and EtOH was distilled off until the internal temperature was above 100° C. More ethanol was then introduced, and this was again distilled off. The procedure was repeated until only the diester was present according to TLC. Finally, all the ethanol was taken off, the crude product obtained was taken up in ethyl acetate, extracted with aqueous $NaHCO_3$ solution and, after phase separation and drying, all the solvent was again taken off. The solid which solidified during this procedure could be purified, after breaking up, by stirring with hexane. This gave 190.4 g (78%) of light yellow crystals.

Melting point: 61–63° C.; $^1H$ NMR ($CDCl_3$); δ [ppm]= 8.00 (s; 1H, H-aryl), 7.34 (s, 1H, H-aryl), 4.43+4.37 (each q, 2+2H, $OCH_2$, J=7.5 Hz), 3.92 (s, 3H, O—Me), 1.42+1.38 (each t, 3+3H, $CH_3$, J=7.5 Hz).

B. Synthesis of Compounds of the Formula (III)

EXAMPLE B1

Synthesis of 4-Hexyloxybenzeneboronic Acid a) Synthesis of 4-Hexyloxybromobenzene:

4-bromophenol (173 g, 1 mol) was dissolved in about 500 ml of freshly distilled THF under protective gas and, after passing argon through the mixture, NaH (33 g (80% strength in oil), 1.1 mol) was added a little at a time. During this procedure, the clear solution became a turbid gray and the temperature increased by 20°. The suspension was stirred at room temperature for about 1 hour under a blanket of protective gas. Hexyl bromide (181 g; 149 ml; 1.1 mol) was placed in a dropping funnel, $N_2$ was briefly passed through it and it was added while stirring over a period of 25 minutes. The still gray mixture was refluxed at 75° C. After 3 days (the suspension had now become lighter in color), the salt formed was filtered off with suction and the filtrate was treated with 20 ml of EtOH (no gas evolution) to destroy any remaining NaH. The yellow solution was evaporated and the product was isolated from the (turbid) solution by means of fractional vacuum distillation: product: 95° C./1 mbar; 172.5 g 67%); (d~1.17).

$^1H$ NMR (400 MHz; $CDCl_3$); δ [ppm]=7.35, 6.76 (AA'BB'; 4H; H-aryl), 3.91 (t; 2H; J=7.5 Hz; O—$CH_2$), 1.77 (pseudo-quin; 2H; J=7.3 Hz; O—$CH_2$—$CH_2$), 1.45–1.25 (m; 6H; H-alkyl), 0.91 (pseudo-t; 3H; J=7.7 Hz; $CH_3$).

b) Synthesis of 4-Hexyloxybenzeneboronic Acid:

In an apparatus which had been baked out and blanketed with argon, magnesium turnings (1.89 g; 78 mmol) were treated with a crystal of iodine and covered with dried THF. A few drops of 4-hexyloxybromobenzene were then added to the solution without stirring. The Grignard reaction began very quickly and, while stirring, the 4-hexyloxybromobenzene (total amount: 20 g; 78 mmol) was then added dropwise at such a rate that the mixture boiled gently. During this addition, the mixture was diluted with a little THF (total amount: about 100 ml). The mixture was refluxed for 3 hours (only a few flakes of magnesium remaining in the solution) and subsequently allowed to cool. The Grignard solution was transferred to a 250 ml dropping funnel in a countercurrent of protective gas and added dropwise to a solution of trimethyl borate (8.9 g; 9.6 ml; 86 mmol) in 50 ml of dry THF while stirring at −70° C., resulting in formation of a precipitate. The reaction mixture was allowed to warm to RT overnight and was then introduced while stirring into a mixture of 100 g of ice and 3 ml of concentrated sulfuric acid. The organic phase was separated off, the aqueous phase was extracted 3 times with 100 ml each time of chloroform and the combined organic phases were evaporated. The crude product was subsequently recrystallized from hexane. Product: colorless, wax-like solid (11.28 g; 66%); melting point: 84–87° C.
$^1$H NMR (400 MHz; CDCl$_3$); δ [ppm]=8.15, 7.00 (AA'BB'; 4H; H-aryl), 4.07 (t; 2H; J=7.7 Hz; O—CH$_2$), 1.83 (pseudo-quin; 2H; J=7.5 Hz; O—CH$_2$—CH$_2$), 1.55–1.32 (m; 6H; H-alkyl), 0.93 (pseudo-t; 3H; J=7.7 Hz; CH$_3$). Contains variable proportions of anhydrides.

EXAMPLE B2

Synthesis of 3-(3,7-Dimethyloctyloxy)benzeneboronic Acid a) Synthesis of 3-(3,7-Dimethyloctyloxy)bromobenzene:

450 ml of ethanol were placed in a reaction vessel and NaI (10.5 g; 70 mmol) and KOH (67.3 g; 1.2 mol) were added. After the addition of KOH, a temperature rise from 25 to 40° C. was observed. After cooling to room temperature, 3-bromophenol (176.5 g; 1 mol) was added. The white suspension became beige during this addition. 3,7-dimethyloctyl chloride (186.32 g; 212.94 ml; 1.05 mol) was added via a dropping funnel over a period of 3 minutes. The mixture was stirred for another 2 hours at RT and subsequently stirred for 96 hours at an internal temperature of 80° C. Ethanol was distilled off. The residue was taken up in ethyl acetate and the precipitate was separated off by filtration. The organic phase was extracted three times with 10% strength by weight aqueous NaOH solution, washed once with H$_2$O, washed three times with H$_2$O which had been acidified with CO$_2$ and washed once more with H$_2$O. After drying over MgSO$_4$, the solvent was again taken off on a rotary evaporator and the crude product was purified by fractional vacuum distillation.

Product: high-boiling colorless oil; 180° C. at 2–3 mbar; 262.3 g (84%); $^1$H NMR (400 MHz; CDCl$_3$); δ [ppm]=7.12 (pseudo-t; 1H; J=8 Hz; H-5), 7.05 (m; 2H; H-2, H-6), 6.81 (ddd; 1H; J$_1$=8, J$_2$=2, J$_3$=0.7 Hz; H-4), 3.97 (m; 2H; O—CH$_2$), 1.81 (m; 1H; O—CH$_2$—CH$_2$—CH), 1.70–1.50 (m; 3H; H-alkyl), 1.35–1.13 (m; 6H; H-alkyl), 0.93 (d; 3H; J=7.7 Hz; CH$_3$), 0.87 (d; 6H; J=7.7 Hz; CH$_3$).

b) Synthesis of 3-(3,7-Dimethyloctyloxy)benzeneboronic Acid:

Mg turnings (24.7 g, 1.02 mol) were placed in a reaction vessel and the apparatus was baked out under argon. At room temperature, about 100 ml of THF were introduced via a dropping funnel and a few crystals of iodine were added. Without stirring, a few ml of 3-(3,7-dimethyloctyloxy)bromobenzene were subsequently added dropwise to the solution and heating was applied at the point of addition by means of a hot air blower. After the reaction had started, the remaining 3-(3,7-dimethyloctyloxy)bromobenzene (total amount: 313 g, 1 mol, 280 ml) was continuously run in dropwise while stirring (70 min). At the same time, a further 1100 ml of THF were added. The reaction mixture was stirred for another 2 hours under reflux.

After cooling to room temperature, the resulting Grignard reagent was added dropwise, under protective gas and with rapid stirring, to a mixture of 800 ml of THF and 123 ml of trimethyl borate (114 g, 1.10 mol) which had been cooled to −70° C. The Grignard reagent was added at such a rate that the internal temperature did not exceed −60° C. (time: 3 hours). A light-colored suspension was formed.

The reaction mixture was stirred into 1200 g of ice water/40 ml of concentrated H$_2$SO$_4$. The clear phases were separated and the aqueous phase was shaken with ethyl acetate. The combined organic phases were stirred with water and, after drying, evaporated.

For further purification, the colorless solid obtained in this way was stirred with about 500 ml of hexane (which had been admixed with 2 ml of concentrated aqueous HCl).

This gave 239 g (86%) of colorless, crystalline powder.

Melting point: 83–89° C. $^1$H NMR 400 MHz; CDCl$_3$); δ [ppm]=7.81 (td; 1H; J$_1$=8, J$_2$=1.3 Hz; H-4), 7.73 (dd; 1H; J$_1$=2, J$_2$=1.1 Hz; H-2), 7.43 (t; 1H; J=8 Hz; H-5), 7.13 (ddd; 1H; J$_1$=8, J$_2$=2, J$_3$=1.1 Hz; H-6), 4.11 (m; 2H; O—CH$_2$), 1.90 (m; 1H; O—CH$_2$—CH$_2$—CH), 1.75–1.50 (m; 3H; H-alkyl), 1.44–1.14 (m; 6H; H-alkyl), 1.00 (d; 3H; J=7.9 Hz; CH$_3$), 0.88 (d; 6H; J=7.8 Hz; CH$_3$). Contains variable proportions of anhydrides.

EXAMPLE B3

Synthesis of 2,5-Dimethylbenzeneboronic Acid

Magnesium turnings (13.3 g; 0.55 mol) are introduced into a baked-out, argon-blanketed apparatus, covered with about 30 ml of THF and a few crystals of iodine are added. Without stirring, a few drops of bromo-p-xylene (cf. Example A1 a)) were subsequently added to the solution. The Grignard reaction began very quickly and the remaining bromo-p-xylene (total amount: 92.59; about 70 ml; 0.5 mol) was subsequently added dropwise while stirring. The mixture was refluxed for 4 hours and then cooled. The Grignard solution was then transferred in a countercurrent of protective gas into a 500 ml dropping funnel and added dropwise to a solution of trimethyl borate (62.4 g; 67 ml; 0.6 mol) in 350 ml of THF while stirring at −70° C. (time: about 1 hour). A precipitate was formed during this addition. The reaction mixture was allowed to warm to RT overnight and was then introduced while stirring into a mixture of 700 g of ice and 20 ml of concentrated sulfuric acid. The organic phase was separated off, the aqueous phase was extracted three times with chloroform and the combined organic phases were evaporated. The crude product was recrystallized from chloroform/hexane. This gave a colorless microcrystalline powder: 47.71 g (64%).

$^1$H NMR (400 MHz; CDCl$_3$); δ [ppm]=800 (d; 1H; J=1.4 Hz; H-6), 7.26 (dd; 1H; J$_1$=8.0, J$_2$=1.4 Hz; H-4), 7.17 (d; 1H; J=8 Hz; H-3), 2.76, 2.38 (each: s; 3H; CH$_3$). Contains variable proportions of anhydrides.

EXAMPLE B4

Synthesis of 4-(3,7-Dimethyloctyloxy)benzeneboronic Acid a) Synthesis of 4-(3,7-Dimethyloctyloxy)bromobenzene
Procedure analogous to Example B2, a).
Yield: 85%; Boiling point: 180° C. at 2 mbar; $^1$H NMR (CDCl$_3$); δ [ppm]=7.36, 6.77 (AA'BB', 4H, H-aryl), 3.95 (m, 2H, O—CH$_2$), 1.82 (m, 1H, H-3'), 1.6 (m, 3H, H-2', H-7'), 1.24 (m, 6H, H-4', H-5, H-6'), 0.94 (d, 3H, Me, J=7 Hz), 0.87 (d, 6H, Me, J=7 Hz).

b) Synthesis of 4-(3,7-Dimethyloctyloxy)benzeneboronic Acid

Procedure analogous to Example B2, b).

Yield: 83%; Melting point: 57–63° C.; $^1$H NMR (CDCl$_3$); δ [ppm]=7.67, 6.92 (AA'BB', 4H, H-aryl), 4.6 (br, 2H, B(OH)$_2$), 4.03 (m, 2H, O—CH$_2$), 1.87 (m, 1H, H-3'), 1.65 (m, 3H, H-2', H-7'), 1.27 (m, 6H, H-4', H-5', H-6'), 0.95 (d, 3H, Me, J=7 Hz), 0.87 (d, 6H, Me, J=7 Hz). Contains variable proportions of anhydrides.

EXAMPLE B5

Synthesis of 3,4-bis(2-Methylpropyloxy) benzeneboronic Acid a) Synthesis of 1,2-bis(2-Methylpropyloxy)benzene:

Catechol (220.22 g, 2 mol), NaI (10.49 g, 0.14 mol) and 900 ml of ethanol were placed in a reaction vessel and heated to reflux. Subsequently, KOA (56.11 g, 1 mol) dissolved in about 300 ml of ethanol, and at the same time, 1-bromo-2-methylpropane (137.03 g, 1 mol, 108.75 ml) were slowly added dropwise. The mixture was refluxed overnight. On the next day, the same amounts of KOH and alkyl bromide were again added. This procedure was repeated a total of 7 times. After cooling the reaction mixture, the solution was decanted from the solid. The filter cake was washed with ethanol. The organic phase was evaporated. The filter cake was dissolved in 1 l of warm water and admixed with the organic phase diluted with ethyl acetate. After phase separation, the organic phase was repeatedly stirred with 10% strength aqueous NaOH, washed with water and dried over Na$_2$SO$_4$. The crude product obtained after taking off the solvent was fractionally distilled under reduced pressure.

The product was obtained as a colorless oil (boiling point: 82° C. at 0.18 mbar): 333.4 g (75%).

$^1$H NMR (CDCl$_3$); δ [ppm]=6.87, (ps-s, 4H, H-aryl), 3.75 (d, 4H, O—CH$_2$, J=8 Hz), 2.13 (ps-non, 2H, C—H, J=8 Hz), 1.05 (d, 12H, CH$_3$, J=8 Hz).

b) Synthesis of 3,4-bis(2-Methylpropyloxy)bromobenzene:

1,2-bis(2-methylpropyloxy)benzene (359.61 g, 1.62 mol) together with 500 ml of CH$_2$Cl$_2$ were placed in a reaction vessel and a little iron powder was added. While cooling, bromine (266.88 g, 1.78 mol) (mixed with about 200 ml of CH$_2$Cl$_2$) was then slowly added dropwise. The mixture was stirred for about 20 hours at room temperature. The mixture was worked up by stirring with aqueous Na$_2$SO$_3$ solution and subsequently filtering off the iron powder. The organic phase was then shaken twice with NaHCO$_3$ solution and subsequently washed with water until neutral. After drying, the organic phase was evaporated.

The crude product was fractionally distilled twice to give the desired product as a colorless solid (166.9 g, 34%).

Melting point: 47° C.; $^1$H NMR (CDCl$_3$); δ [ppm]=6.98 (m, 2H, H-2, H-6), 6.73 (m, 1H, H-5), 3.72, 3.70 (2×d, 2×2H, O—CH$_2$, J=8 Hz), 2.12 (m, 2H, CH), 1.04 (m, 12H, CH$_3$).

c) Synthesis of 3,4-bis(2-Methylpropyloxy)benzeneboronic Acid:

Procedure analogous to Example B2, b).

Yield: 76%; Melting point: 146° C. $^1$H NMR (CDCl$_3$); δ [ppm]=7.81 (dd, 1H, H-6, J$_1$=8 Hz, J$_2$=1.8 Hz), 7.68 (d, 1H, H-2, J=1.8 Hz), 6.99 (d, 1H, H-5, J=8 Hz), 3.89, 3.84 (2×d, 2×2H, O—CH$_2$, J=8 Hz), 2.13 (m, 2H, CH), 1.07 (m, 12H, CH$_3$). Contains variable proportions of anhydrides.

EXAMPLE B6

Synthesis of 4-(3,7-Dimethyloctyloxy)biphenyl-4-boronic Acid a) Synthesis of 4-(3,7-Dimethyloctyloxy)-4'-bromobiphenyl:

Procedure analogous to Example B2, a).

Work-up by recrystallization from ethanol.

Colorless crystals, 85% yield. Melting point: 104° C.; $^1$H NMR (CDCl$_3$); δ [ppm]=7.53, 7.40 (AA'BB', 4H, H-aryl), 7.47, 6.96 (AA'BB', 4H, H-aryl), 4.03 (m, 2H, O—CH$_2$), 1.83 (m, 1H, H-3'), 1.62 (m, 3H, H-2', H-7'), 1.3 (m, 6H, H-4', H-5', H-6'), 0.96 (d, 3H, Me, J=7.5 Hz), 0.87 (d, 6H, Me, J=7.5 Hz).

b) Synthesis of 4'-(3,7-Dimethyloctyloxy)biphenyl-4-boronic Acid:

Procedure analogous to Example B2, b).

Yield: 78%; Melting point: 116° C.; $^1$H NMR (DMSO); δ [ppm]=8.02 (br, 2H, B(OH)$_2$), 7.83, 7.58 (AA'BB', 4H, H-aryl), 7.61, 7.01 (AA'BB', 4H, H-aryl), 4.04 (m, 2H, O—CH$_2$), 1.77 (m, 1H, H-3'), 1.58 (m, 3H, H-2', H-7'), 1.25 (m, 6H, H-4', H-5', H-6'), 0.92 (d, 3H, Me, J=7.5 Hz), 0.86 (d, 6H, Me, J=7.5 Hz).

C. Coupling Reactions by Reaction A

EXAMPLE C1

Synthesis of Diethyl 2-(4'-Hexyloxyphenyl) terephthalate

Diethyl bromoterephthalate (30.1 g, 100 mmol), K$_2$CO$_3$ (27.6 g, 200 mmol) and 140 ml of toluene and 140 ml of H$_2$O were placed in a reaction vessel and argon was passed in for 30 minutes. 4-hexyloxyphenylboronic acid (26.7 g, 120 mmol) (cf. B1) and Pd(PPh$_3$)$_4$ (1.16 g, 1 mmol) were subsequently added under protective gas. The yellow-green, turbid mixture was stirred vigorously under a blanket of protective gas at an internal temperature of 85° C. After 7 hours, the reaction was complete. After phase separation, the organic phase was shaken with dilute HCl/H$_2$O (until neutral). The aqueous phase was shaken with toluene and the organic phases were combined. After filtering off any palladium residues, the solution was evaporated. The product was obtained as a yellowish brown oil in sufficient purity (about 85%): 44.7 g (1112%).

$^1$H NMR (400 MHz; CDCl$_3$): δ [ppm]=8.03 (dd; 1H; J$_1$=2, J$_2$=1 Hz; H-3), 8.02 (dd; 1H; J$_1$=8, J$_2$=2 Hz; H-5), 7.79 (dd; 1H; J$_1$=8, J$_2$=1 Hz; H-6), 7.25, 6.93 (AA'BB'; 4H; H-phenyl), 4.40, 4.14 (each: q; 2H; J=8 Hz; CO$_2$—CH$_2$), 3.99 (t; 2H; J=7.5 Hz; O—CH$_2$), 1.81 (m; 2H; O—CH$_2$—CH$_2$), 1.53–1.33 (m; 6H; H-alkyl), 1.40, 1.07 (each: t; 3H; J=8 Hz; CO$_2$—CH$_2$—CH$_3$), 0.91 (m; 3H; CH$_3$).

EXAMPLE C2

Synthesis of Dimethyl 2-(3'-(3,7-Dimethyloctyloxy) phenyl)terephthalate

Dimethyl bromoterephthalate (49.7 g, 182 mmol, from TransWorld, Rockville Md., USA, or prepared by a method similar to Example A1 c)), K$_2$CO$_3$ (50.3 g, 364 mmol) and 170 ml of toluene and 170 ml of H$_2$O were placed in a reaction vessel and argon was passed in for 30 minutes. 3-(3,7-dimethyloctyloxy)boronic acid (55.7 g, 200 mmol) (cf. B2) and Pd(PPh$_3$)$_4$ (0.93 g, 0.8 mmol) were then added under protective gas. The yellow-green, turbid mixture was stirred vigorously under a blanket of protective gas at an internal temperature of 85° C. After 24 hours, the reaction was complete. After phase separation, the organic phase was shaken with dilute $HCl/H_2O$ (until neutral). The aqueous phase was shaken with ethyl acetate and the organic phases were combined. These were evaporated and dried at 2 mbar. The product was obtained as a yellow oil in sufficient purity (greater than 95%): 76.1 g (98%).

$^1H$ NMR (400 MHz; $CDCl_3$): δ [ppm]=8.07 (d; 1H; J=2 Hz; H-3), 8.05 (dd; 1H; $J_1$=8, $J_2$=2 Hz; H-5), 7.82 (d; 1H; J=8 Hz; H-6), 7.29 (t; 1H; J=8 Hz; H-5'), 6.90 (m; 3H; H-2', H-4', H-6'), 4.01 (m; 2H; O—$CH_2$), 3.94, 3.67 (each: s; 3H; $CO_2$—$CH_3$), 1.84 (m; 1H; O—$CH_2$—$CH_2$—CH), 1.63–1.48 (m; 3H; H-alkyl), 1.37–1.12 (m; 6H; H-alkyl), 0.96 (d; 3H; J=7.8 Hz; $CH_3$), 0.87 (d; 6H; J=7.7 Hz; $CH_3$).

EXAMPLE C3

Synthesis of Diethyl 2-(2',5'-Dimethylphenyl)terephthalate

Diethyl bromoterephthalate (45.2 g, 150 mmol), $K_2CO_3$ (41.5 g, 300 mmol), 140 ml of toluene and 140 ml of $H_2O$ were placed in a reaction vessel and argon was passed in for 30 minutes. 2,5-dimethylbenzeneboronic acid (24.8 g, 165 mmol) (cf. B3) and $Pd(PPh_3)_4$ (0.7g, 0.6 mmol) were subsequently added under protective gas. The brownish mixture, which was turbid due to phase separation, was stirred vigorously under a blanket of protective gas at an internal temperature of 85° C. The reaction was complete after 24 hours (according to TLC). After phase separation, the organic phase was shaken with dilute $HCl/H_2O$ (until neutral). The aqueous phase was shaken with toluene and the organic phases were combined. After filtering off any palladium residues, the solution was evaporated. The product was obtained as a yellow oil in sufficient purity (greater than 97%). Yield: 48.7 g (99%).

$^1H$ NMR (400 MHz; $CDCl_3$): δ [ppm]=8.07 (dd; 1H; $J_1$=8, $J_2$=2 Hz; H-5), 7.96 (d; 1H; J=8 Hz; H-6), 7.92 (d; 1H; J=2 Hz; H-3), 7.14 (d; 1H; J=7.9 Hz; H-3'), 7.09 (dd; 1H; $J_1$=7.9, $J_2$=2 Hz; H-4'), 6.91 (d; 1H; J=2 Hz; H-6'), 4.39, 4.16 (each: q; 2H; J=8 Hz; $CO_2$—$CH_2$), 2.32, 2.02 (each: s; 3H; aryl-$CH_3$), 1.39, 0.97 (each: t; 3H; J=8 Hz; $CO_2CH_2$—$CH_3$).

EXAMPLE C4

Synthesis of Diethyl 4'-(3",7"-Dimethyloctyloxy)terephthalate

Procedure analogous to Example C3; palladium residues were removed by stirring with 1% strength aqueous NaCN solution.

The product (100% yield) is a colorless, highly viscous oil.

$^1H$ NMR ($CDCl_3$): δ [ppm]=8.04 (d, 1H, H-3, J=1.8 Hz), 8.03 (dd, 1H, H-5, $J_1$=7.8, $J_2$=1.8 Hz), 7.8 (d, 1H, H-6, J=7.8 Hz), 7.25, 6.93 (AA'BB', 4H, H-aryl), 4.40, 4.15 (2×q, 2×2H, $CO_2CH_2$, J=7.6 Hz), 4.04 (m, 2H, O—$CH_2$), 1.86 (m, 1H, H-3"), 1.60 (m, 3H, H-2", H-7"), 1.40, 1.07 (2×t, 2×3H, ester-$CH_3$, J=7.6 Hz), 1.30 (m, 6H, H-4", H-5", H-6"), 0.92 (d, 3H, Me, J=7.5 Hz), 0.86 (d, 6H, Me, J=7.5 Hz).

EXAMPLE C5

Synthesis of Diethyl 3,4-bis(2-Methylpropyloxy)phenylterephthalate

Synthesis analogous to Example C4. The product (99% yield) is a colorless, highly viscous oil.

$^1H$ NMR ($CDCl_3$): δ [ppm]=8.05 (d, 1H, H-3, J=1.9 Hz), 8.03 (dd, 1H, H-5, $J_1$=7.9, $J_2$=1.9 Hz), 7.77 (d, 1H, H-6, J=7.9 Hz), 6.87 (m, 3H, H-aryl), 4.40, 4.13 (2×q, 2×2H, $CO_2CH_2$, J=7.5 Hz), 3.79, 3.76 (2×d, 2×2H, O—$CH_2$, J=8 Hz), 2.13 (m, 2H, CH), 1.41, 1.07 (2×t, 2×3H, ester-$CH_3$, J=7.5 Hz), 1.04 (m, 12H, $CH_3$).

EXAMPLE C6

Synthesis of Diethyl 4-[4'-(3,7-Dimethyloctyloxy)biphenyl]terephthalate

Synthesis analogous to Example C4. The product (99% yield) is a colorless, highly viscous oil.

$^1H$ NMR ($CDCl_3$): δ [ppm]=8.10 (d, 1H, H-3, J=1.9 Hz), 8.07 (dd, 1H, H-5, $J_1$=7.9, $J_2$=1.9 Hz), 7.86 (d, 1H, H-6, J=7.9 Hz), 7.59, 7.38 (AA'BB', 4H, H-aryl), 7.56, 6.99 (AA'BB', 4H, H-aryl), 4.41, 4.14 (2×q, 2×2H, $CO_2CH_2$, J=7.6 Hz), 4.05 (m, 2H, O—$CH_2$), 1.86 (m, 1H, H-3"), 1.65 (m, 3H, H-2", H-7"), 1.41, 1.04 (2×t, 2×3H, ester-$CH_3$, J=7.6 Hz), 1.30 (m, 6H, H-4", H-5", H-6"), 0.96 (d, 3H, Me, J=7.5 Hz), 0.87 (d, 6H, Me, J=7.5 Hz).

EXAMPLE C7

Synthesis of Diethyl 2-[4-(3,7-Dimethyloctyloxy)phenyl]-5-methoxyterephthalate

Synthesis analogous to Example C4 (here using diethyl 2-bromo-5-methoxyterephthalate, cf. Example A2). The product (95% yield) was a colorless, highly viscous oil.

$^1H$ NMR ($CDCl_3$): δ [ppm]=7.75, 7.35 (2×s, 2×1H, H-3, H-6), 7.20, 6.91 (AA'BB', 4H, H-aryl), 4.37, 4.12 (2×q, 2×2H, $CO_2CH_2$, J=7.6 Hz), 4.02 (m, 2H, O—$CH_2$), 3.97 (s, 3H, O—Me), 1.84 (m, 1H, H-3"), 1.62 (m, 3H, H-2", H-7"), 1.37, 1.03 (2×t, 2×3H, ester-$CH_3$, J=7.6 Hz), 1.28 (m, 6H, H-4", H-5", H-6"), 0.96 (d, 3H, Me, J=7.5 Hz), 0.87 (d, 6H, Me, J=7.5 Hz).

EXAMPLE C8

Synthesis of Diethyl 2-[3-(3,7-Dimethyloctyloxy)phenyl]-5-methoxyterephthalate

Synthesis analogous to Example C7. The product (95% yield) was a colorless, highly viscous oil.

$^1H$ NMR ($CDCl_3$): δ [ppm]=7.78, 7.37 (2×s, 2×1H, H-3, H-6), 7.26 (t; 1H; H-5', J=8 Hz), 6.86 (m; 3H; H-2', H-4', H-6'), 4.37, 4.10 (2×q, 2×2H, $CO_2CH_2$, J=7.6 Hz), 4.00 (m, 2H, O—$CH_2$), 3.97 (s, 3H, O—Me), 1.83 (m, 1H, H-3"), 1.62 (m, 3H, H-2", H-7"), 1.37, 1.02 (2×t, 2×3H, ester-$CH_3$, J=7.6 Hz), 1.28 (m, 6H, H-4", H-5", H-6"), 0.95 (d, 3H, Me, J=7.5 Hz), 0.86 (d, 6H, Me, J=7.5 Hz).

D. Reductions by Reaction B

EXAMPLE D1

Synthesis of 2,5-Bishydroxymethyl-4'-hexyloxybiphenyl $LiAlH_4$ (5.3 g, 140 mmol) and about 200 ml of THF were blanketed with argon in a reaction vessel and diethyl 2-(4'-hexyloxyphenyl)terephthalate (40 g, 100 mmol) (cf. C1) together with a further 50 ml of THF were slowly added dropwise from a dropping funnel. The reaction mixture was stirred vigorously during this addition. The mixture was subsequently refluxed for about one hour. The reaction mixture was brought to RT and, while cooling in a water bath and blanketing with argon, ice water was carefully added dropwise until gas evolution had ceased. Dilute (10% strength) sulfuric acid was subsequently added dropwise until the turbid gray mixture was clear. The phases were separated by addition of chloroform and the aqueous phase was shaken twice with chloroform. The organic phases were washed once with $H_2O$ and subsequently evaporated. The crude product obtained was recrystallized from hexane/ethyl acetate (5:1).

Product: 20.3 g (65%) of colorless needles, purity>98%. Melting point: 72.5–74° C.

$^1$H NMR (400 MHz; $CDCl_3$): δ [ppm]=7.53 (d; 1H; J=8 Hz; H-6), 7.36 (dd; 1H; $J_1$=8, $J_2$=2 Hz; H-5), 7.27 (d; 1H; J=2 Hz; H-3), 7.26, 6.94 (AA'BB'; 4H; H-phenyl), 4.72, 4.61 (each: s; 2H; $CH_2$—O), 3.99 (t; 2H;

J=7.5 Hz; O—$CH_2$), 1.81 (m; 2H; O—$CH_2$—$CH_2$), 1.53–1.26 (m; 6H; H-alkyl), 0.92 (m; 3H; $CH_3$).

EXAMPLE D2

Synthesis of 2,5-Bishydroxymethyl-3'-(3,7-dimethyloctyloxy)biphenyl $LiAlH_4$ (9.4 g, 248 mmol) and 300 ml of THF were placed in a reaction vessel under $N_2$. At RT, dimethyl 2-(3'-(3,7-dimethyl-octyloxy)phenyl)terephthalate (75.5 g, 177 mmol), dissolved in 120 ml of THF, was then slowly added dropwise. The mixture was subsequently stirred for 4 hours under reflux. After cooling, excess $LiAlH_4$ was carefully destroyed by addition of $H_2O$. Half-concentrated $H_2SO_4$ (about 50 ml) was then carefully added dropwise. The mixture became very viscous during this addition. After stirring further for 1 hour, a clear solution and, at the bottom of the flask, a slimy gray precipitate could be seen. The clear solution was decanted off and the solvent was taken off. The precipitate which remained was stirred with plenty of water and ethyl acetate, the organic phase was separated off after filtration, the solvent was taken off and combined with the first organic phase. The combined organic phases were taken up in ethyl acetate and extracted five times with water. After drying over $MgSO_4$, the solvent was taken off. The resulting oil was stirred a number of times with hexane and dried in an oil pump vacuum. The product was obtained as a pure, light yellow, highly viscous oil (54 g, 82%).

$^1$H NMR (400 MHz; $CDCl_3$): δ [ppm]=7.50 (d; 1H; J=7.8 Hz; H-6), 7.34 (dd; 1H; $J_1$=7.8, $J_2$=1.9 Hz; H-5), 7.30 (dt; 1H; $J_1$=8, $J_2$=1 Hz; H-5'), 7.26 (d; 1H; J=1.9 Hz; H-3), 6.88 (m; 3H; H-2', H-4', H-6'), 4.69, 4.59 (each: s; 2H; $CH_2$—OH), 4.00 (m; 2H; O—$CH_2$), 1.97 (s; 2H; OH), 1.82 (m; 1H; O—$CH_2$—$CH_2$—CH), 1.67–1.50 (m; 3H; H-alkyl), 1.40–1.13 (m; 6H; H-alkyl), 0.95 (d; 3H; J=7.5 Hz; $CH_3$), 0.87 (d; 6H; J=7.6 Hz; $CH_3$).

EXAMPLE D3

Synthesis of 2,5-Bishydroxymethyl-2',5'-dimethylbiphenyl $LiAlH_4$ (7.9 g, 208 mmol) together with about 250 ml of THF were placed in a reaction vessel under a blanket of argon. Diethyl 2-(2',5'-dimethylphenyl)terephthalate (48.6 g, 149 mmol) (cf. C3) was diluted in a dropping funnel with about 60 ml of THF and slowly added dropwise. The reaction mixture was stirred vigorously during this addition. The mixture was diluted with another 100 ml of THF and then refluxed at 67° C. After 2 hours, it was cooled to RT. While cooling on a water bath and blanketing with argon, ice water was added dropwise until gas evolution had ceased. Dilute (10% strength) sulfuric acid was subsequently added dropwise until the turbid gray mixture became clear. The phase mixture was separated by addition of a generous amount of chloroform and the aqueous phase was subsequently shaken twice with chloroform. The organic phases were shaken once with $H_2O$ and evaporated. The crude product was recrystallized from chloroform/hexane: 24.7 g (68%) of colorless, microcrystalline powder; melting point: 145–148° C. (purity>95%).

$^1$H NMR (400 MHz; $CDCl_3$): δ [ppm]=7.54 (d; 1H; J=7.8 Hz; H-6), 7.38 (dd; 1H; $J_1$=7.8, $J_2$=1.8 Hz; H-5), 7.15 (d; 1H; J=7.8 Hz; H-3'), 7.13 (d; 1H; J=1.9 Hz; H-3), 7.08 (dd; 1H; $J_1$=7.7, $J_2$=1.5 Hz; H-4'), 6.94 (d; 1H; J=1.5 Hz; H-6'), 4.72, 4.42 (each: s; 2H; $CH_2$—O), 2.33, 2.01 (each: s; 3H; aryl-$CH_3$).

EXAMPLE D4

Synthesis of 2,5-Bishydroxymethyl-4-(3,7-dimethyloctyloxy)biphenyl

Procedure analogous to Example D3; however, the reaction mixture was worked up under alkaline rather than acid conditions: for this purpose, x ml of water (when using x g of $LiAlH_4$) were carefully added after the reduction was complete. Subsequently, x ml of aqueous NaOH solution (15% strength) and finally 3 x ml of water were added. After each addition, the mixture was stirred for about 15 minutes ("1:1:3 method"). The solution was filtered with suction from the solid formed, the latter was again stirred with THF and the combined organic phases were finally evaporated. This work-up was found to be more advantageous than the acid variant which was employed in Examples D1 to D3. Recrystallization from hexane/ethyl acetate (30:1).

The product (88% yield) was obtained as a colorless, wax-like solid.

Melting point: 67° C.; $^1$H NMR ($CDCl_3$): δ [ppm]=7.53 (d, 1H, H-6, J=7.9 Hz), 7.36 (dd, 1H, H-5, $J_1$=7.9, $J_2$=2 Hz), 7.27 (d, 1H, H-3, J=2 Hz), 7.28, 6.95 (AA'BB', 4H, H-aryl), 4.72, 4.63 (2×d, 2×2H, $CH_2$O, J=8 Hz), 4.03 (m, 2H, O—$CH_2$), 1.90, 1.68 (2×t, 2×1H, OH, J=8 Hz), 1.85 (m, 1H, H-3'), 1.65 (m, 3H, H-2', H-7'), 1.30 (m, 6H, H-4', H-5', H-6'), 0.97 (d, 3H, Me, J=7.5 Hz), 0.87 (d, 6H, Me, J=7.5 Hz).

EXAMPLE D5

Synthesis of 2,5-Bishydroxymethyl-3',4'-bis(2-methylpropyloxy)biphenyl

Synthesis analogous to Example D4. Recrystallization from hexane/ethyl acetate (15:1). The product (84% yield) was obtained as colorless crystals.

Melting point: 73° C.; $^1$H NMR ($CDCl_3$): δ [ppm] 7.53 (d, 1H, H-6, J=7.9 Hz), 7.37 (dd, 1H, H-5, $J_1$=7.9, $J_2$=2 Hz), 7.29 (d, 1H, H-3, J=2 Hz), 6.89 (m, 3H, H-aryl), 4.73, 4.63 (2×s, 2×2H, $CH_2$O), 3.80, 3.77 (2×d, 2×2H, O—$CH_2$, J=8 Hz), 2.15 (m, 2H, CH), 1.55 (br, 2H+$H_2$O, OH), 1.06, 1.03 (2×t, 2×6H, $CH_3$).

EXAMPLE D6

Synthesis of 2,5-Bishydroxymethyl-4''-(3,7-dimethyloctyloxy)terphenyl

Synthesis analogous to Example D4. Recrystallization from hexane/ethyl acetate (15:1). The product (88% yield) was obtained as colorless crystals.

Melting point: 106° C.; $^1$H NMR ($CDCl_3$): δ [ppm]=7.60, 7.41 (AA'BB', 4H, H-aryl), 7.56, 6.99 (AA'BB', 4H, H-aryl), 7.54 (d, 1H, H-6, J=7.9 Hz), 7.39 (dd, 1H, H-5, $J_1$=7.9, $J_2$=2 Hz), 7.32 (d, 1H, H-3, J=2 Hz), 4.74, 4.66 (2×d, 2×2 H, $CH_2O$, J=4 Hz), 4.05 (m, 2H, O—$CH_2$), 1.87 (m, 1H, H-3'), 1.77, 1.67, (2×br, 2×1H, OH), 1.65 (m, 3H, H-2', H-7'), 1.27 (m, 6H, H-4', H-5', H-6'), 0.96 (d, 3H, Me, J=7.5 Hz), 0.88 (d, 6H, Me, J=7.5 Hz).

EXAMPLE D7

Synthesis of 2,5-Bishydroxymethyl-4-methoxy-4'-(3,7-dimethyloctyloxy)biphenyl

Synthesis analogous to Example D4. Recrystallization from hexane/ethyl acetate (20:1). The product (93% yield) was obtained as colorless crystals.

Melting point: 101° C.; $^1$H NMR (CDCl$_3$): δ [ppm]=7.21, 6.93 (AA'BB', 4H, H-aryl), 7.18, 7.10 (2×s, 2×1H, H-3, H-6), 4.70, 4.62 (2×s, 2×2H, $CH_2O$), 4.02 (m, 2H, O—$CH_2$), 3.93 (s, 3H, O—Me), 1.85 (m, 1H, H-3'), 1.65 (br, 2H, OH), 1.60 (m, 3H, H-2', H-7'), 1.28 (m, 6H, H-4', H-5', H-6'), 0.96 (d, 3H, Me, J=7.5 Hz), 0.86 (d, 6H, Me, J=7.5 Hz).

EXAMPLE D8

Synthesis of 2,5-Bishydroxymethyl-4-methoxy-3'-(3,7-dimethyloctyloxy)biphenyl

Synthesis analogous to Example D4. Stirring with hot hexane. The product (99% yield) was obtained as a colorless, wax-like solid.

Melting point: 55° C.; $^1$H NMR (CDCl$_3$): δ [ppm]=7.29 (t; 1H; J=8 Hz; H-5), 7.21, 7.12 (2×s, 2×1H, H-3, H-6), 6.87 (m; 3H; H-2', H-4', H-6'), 4.70, 4.64 (2×d, 2×2H, $CH_2O$, J=8 Hz), 4.01 (m, 2H, O—$CH_2$), 3.93 (s, 3H, O—Me), 2.29, 1.63 (2×t, 2×1H, OH, J=8 Hz), 1.84 (m, 1H, H-3'), 1.60 (m, 3H, H-2', H-7'), 1.25 (m, 6H, H-4', H-5', H-6'), 0.94 (d, 3H, Me, J=7.5 Hz), 0.87 (d, 6H, Me, J=7.5 Hz).

E. Halogenations by Reaction C(b)

EXAMPLE E1

Synthesis of 2,5-Bisbromomethyl-4'-hexyloxybiphenyl

While cooling with water, 2,5-bishydroxymethyl-4'-hexyloxybiphenyl (12.6 g, 40 mmol) (cf. D1) was stirred into HBr (33% strength in HAc, 36 ml, 200 mmol). The two-phase, light brown and slightly viscous suspension was stirred overnight at RT under protective gas. The resulting reaction mixture was repeatedly shaken with chloroform until the aqueous phase was colorless. Evaporation of the organic phase gave a clear, honey-colored oil which solidified in the freezer over a period of 1–2 days to give a wax-like, cloudy solid: 16.9 g (96%); melting point: 38.5–40.5° C.; purity>98%.

$^1$H NMR (400 MHz; CDCl$_3$): δ [ppm]=7.49 (d; 1H; J=8 Hz; H-6), 7.35 (dd; 1H; $J_1$=8, $J_2$=2 Hz; H-5), 7.26 (d; 1H; J=2 Hz; H-3), 7.36, 6.98 (AA'BB'; 4H; H-phenyl), 4.48, 4.44 (each: s; 2H; $CH_2$—Br), 4.01 (t; 2H; J=6.5 Hz; O—$CH_2$), 1.81 (quint; 2H; J=6.9 Hz; O—$CH_2$—$CH_2$), 1.50–1.30 (m; 6H; H-alkyl), 0.92 (t; 3H; J=7.0 Hz; $CH_3$). The $^1$H-NMR spectrum shown in FIG. 1 demonstrates the purity of the compound.

EXAMPLE E2

Synthesis of 2,5-Bischloromethyl-4'-hexyloxybiphenyl 2,5-bis(hydroxymethyl)-4'-hexyloxybiphenyl (9.43 g, 30 mmol) (cf. D1) and 50 ml of toluene together with one drop of pyridine (undissolved) were placed in a reaction vessel and SOCl$_2$ was added dropwise over a period of about 10 minutes. After addition of only a few drops, the suspension became clear, associated with a slight increase in temperature. The solution was subsequently stirred at an internal temperature of 60°. After 90 minutes, the mixture was worked up. The reaction mixture was, after cooling, admixed with about 20 ml of water and then shaken with H$_2$O. The aqueous phase was shaken with toluene, the organic phases were combined and evaporated: 10.5 g (100%) of honey-colored, oily product. Purity: about 90% ($^1$H NMR).

$^1$H NMR (400 MHz; CDCl$_3$): δ [ppm]=7.53 (d; 1H; J=8 Hz; H-6), 7.38 (dd; 1H; $J_1$=8, $J_2$=2 Hz; H-5), 7.28 (d; 1H; J=2 Hz; H-3), 7.33, 6.97 (AA'BB'; 4H; H-phenyl), 4.60, 4.53 (each: s; 2H; $CH_2$—Cl), 4.01 (t; 2H); J=6.9 Hz; O—$CH_2$), 1.83 (pseudo-quint; 2H; J=6.9 Hz; O—$CH_2$—$CH_2$), 1.55–1.33 (m; 6H; H-alkyl), 0.94 (m; 3H; $CH_3$).

EXAMPLE E3

Synthesis of 2,5-Bisbromomethyl-2',5'-dimethylbiphenyl 2,5-bishydroxymethyl-2',5'-dimethylbiphenyl (10 g, 41 mmol) (cf. D3) was stirred into HBr (33% strength in HAc, 36 ml, 200 mmol) cooled by means of a water bath. The clear solution was stirred overnight at RT under protective gas. It was shaken a number of times with chloroform until the aqueous phase was colorless. The evaporated organic phase gave a honey-colored oil which did not crystallize even in a freezer (−18° C.): 14.3 g (94%); purity>98%.

$^1$H NMR (400 MHz; CDCl$_3$): δ [ppm]=7.52 (d; 1H; J=7.8 Hz; H-6), 7.37 (dd; 1H; $J_1$=7.8, $J_2$=1.9 Hz; H-5), 7.18 (d; 1H; J=7.8 Hz; H-3'), 7.17 (d; 1H; J=1.9 Hz; H-3), 7.11 (dd; 1H; $J_1$=7.7, $J_2$=1.6 Hz; H-4'), 7.00 (d; 1H; J=1.7 Hz; H-6'), 4.48, 4.28 (each: AB; 2H; $J_{AB}$=12 Hz; $CH_2$Br), 2.35, 2.03 (each: s; 3H; aryl-$CH_3$).

EXAMPLE E4

Synthesis of 2,5-Bischloromethyl-2',5'-dimethylbiphenyl

At room temperature, SOCl$_2$ (36.9 g; 22.7 ml, 310 mmol) was added dropwise to 2,5-bishydroxymethyl-2',5'-dimethylbiphenyl (34.2 g, 141 mmol) over a period of about 20 minutes while stirring under protective gas. At the end of the addition, an oily, slightly turbid solution had been obtained. The reaction mixture was stirred at room temperature for 20 hours, then carefully stirred into 200 ml of aqueous NaHCO$_3$ solution and vigorously stirred with ethyl acetate. After phase separation, the organic phase was shaken with water until neutral and, after drying over Na$_2$SO$_4$, the solvent was finally taken off. Purification was carried out by fractional vacuum distillation over a little NaHCO$_3$. This gave 27.9 g (65%) of product as a clear viscous oil; purity>99% (boiling point: 135° C. at 0.3 mbar).

$^1$H NMR (400 MHz; CDCl$_3$): δ [ppm]=7.56 (d; 1H; J=7.9 Hz; H-6), 7.40 (dd; 1H; $J_1$=7.9, $J_2$=1.8 Hz; H-5), 7.18 (d; 1H; J=1.8 Hz; H-3), 7.16 (d; 1H; J=8 Hz; H-3'), 7.11 (dd; 1H; $J_1$=7.9, $J_2$=1.6 Hz; H-4'), 6.97 (d; 1H; J=1.5 Hz; H-6'), 4.60, 4.35 (each: AB; 2H; $J_{AB}$=12 Hz; $CH_2$—Cl), 2.33, 2.02 (each: s; 3H; aryl-$CH_3$).

The purity of the compound obtained is demonstrated by the $^1$H NMR spectrum shown in FIG. 2.

EXAMPLE E5

Synthesis of 2,5-Bischloromethyl-3'-(3,7-dimethyloctyloxy)biphenyl 2,5-bishydroxymethyl-3'-(3,7-dimethyloctyloxy)biphenyl (50.7 g, 137 mmol) was blanketed with N$_2$ in a reaction vessel and thionyl chloride (20 ml, 274 mmol) was carefully added. A further 2 ml of thionyl chloride were added twice more (after 2 hours and after 8 hours) and the mixture was finally stirred for a total of 20 hours at room temperature. The mixture was carefully poured into aqueous $NaHCO_3$ solution and extracted with ethyl acetate. Finally, the organic phase was washed until neutral. After drying over $MgSO_4$, the ethyl acetate was taken off and the mixture was fractionally distilled under reduced pressure. The product (39 g, 70%) was obtained as a highly viscous, colorless oil (boiling point: 212° C. at 0.67 mbar).

$^1$H NMR (300 MHz; $CDCl_3$): δ [ppm]=7.54 (d; 1H; J=8.3 Hz; H-6), 7.41 (dd; 1H; $J_1$=8.2, $J_2$=2.1 Hz; H-5), 7.34 (d; 1H; $J_1$=8, $J_2$=1 Hz; H-5'), 7.31 (d; 1H; J=2 Hz; H-3), 6.94 (m; 3H; H-2', H-4', H-6'); 4.52 (each: s, 2H; $CH_2Cl$), 4.04 (m; 2H; $O-CH_2$), 1.84 (m; 1H; $O-CH_2-CH_2-CH$), 1.72–1.46 (m; 3H; H-alkyl), 1.38–1.10 (m; 6H; H-alkyl), 0.94 (d; 3H; J=6.7 Hz; $CH_3$), 0.86 (d; 6H; J=6.9 Hz; $CH_3$).

EXAMPLE E6

Synthesis of 2,5-Bischloromethyl-4'-(3,7-dimethyloctyloxy)biphenyl

Procedure analogous to Example E5; the product (67% yield) was obtained by distillation in a short-path still (0.3 mbar, 243° C.) as a colorless, highly viscous oil (purity: 99%).

$^1$H NMR ($CDCl_3$): δ [ppm]=7.52 (d, 1H, H-6, J=7.9 Hz), 7.38 (dd, 1H, H-5, $J_1$=7.9, $J_2$=2 Hz), 7.32, 6.97 (AA'BB', 4H, H-aryl), 7.29 (d, 1H, H-3, J=2 Hz), 4.59, 4.52 (2×s, 2×2H, $CH_2Cl$), 4.04 (m, 2H, $O-CH_2$), 1.85 (m, 1H, H-3'), 1.60 (m, 3H, H-2', H-7'), 1.30 (m, 6H, H-4', H-5', H-6'), 0.97 (d, 3H, Me, J=7.5 Hz), 0.87 (d, 6H, Me, J=7.5 Hz).

EXAMPLE E7

Synthesis of 2,5-Bischloromethyl-3',4'-bis(2-methylpropyloxy)biphenyl

Procedure analogous to Example E5; the product (42% yield) was obtained by distillation in a short-path still (0.5 mbar, 240° C.) as a colorless, highly viscous oil (purity: 99%).

$^1$H NMR ($CDCl_3$): δ [ppm]=7.53 (d, 1H, H-6, J=7.8 Hz), 7.38 (dd, 1H, H-5, $J_1$=7.8, $J_2$=2 Hz), 7.31 (d, 1H, H-3, J=2 Hz), 6.98 (d, 1H, H-2', J=2 Hz), 6.93 (d, 1H, H-5', J=8 Hz), 6.90 (dd, 1H, H-6', $J_1$=8, $J_2$=2 Hz), 4.60, 4.53 (2×s, 2×2H, $CH_2Cl$), 3.80 (m, 4H, $O-CH_2$), 2.16 (m, 2H, CH), 1.07, 1.04 (2×t, 2×6H, $CH_3$, J=7 Hz).

EXAMPLE E8

Synthesis of 2,5-Bischloromethyl-4''-(3,7-dimethyloctyloxy)terphenyl

Procedure analogous to Example E5; the product (25% yield) was obtained by distillation in a short-path still (0.1 mbar, 265° C.) as a colorless, highly viscous oil (purity: >99%).

$^1$H NMR ($CDCl_3$): δ [ppm]=7.65, 7.45 (AA'BB', 4H, H-aryl), 7.58, 7.00 (AA'BB', 4H, H-aryl), 7.56 (d, 1H, H-6, J=8 Hz), 7.43 (dd, 1H, H-5, $J_1$=8, $J_2$=2 Hz), 7.35 (d, 1H, H-3, J=2 Hz), 4.62, 4.57 (2×s, 2×2H, $CH_2Cl$), 4.06 (m, 2H, $O-CH_2$), 1.87 (m, 1H, H-3'), 1.60 (m, 3H, H-2', H-7'), 1.27 (m, 6H, H-4', H-5', H-6'), 0.97 (d, 3H, Me, J=7.5 Hz), 0.87 (d, 6H, Me, J=7.5 Hz).

EXAMPLE E9

Synthesis of 2,5-Bischloromethyl-4-methoxy-4'-(3,7-dimethyloctyloxy)biphenyl

Procedure analogous to Example E5; the product (40% yield) was obtained by distillation in a short-path still (0.3 mbar, 265° C.) as a colorless, highly viscous oil (purity: 99%).

$^1$H NMR ($CDCl_3$): δ [ppm]=7.29, 6.95 (AA'BB', 4H, H-aryl), 7.27, 7.03 (2×s,2×1H, H-3, H-6), 4.65, 4.53 (2×s, 2×2H, $CH_2Cl$), 4.04 (m, 2H, $O-CH_2$), 3.94 (s, 3H, O—Me), 1.85 (m, 1H, H-3'), 1.63 (m, 3H, H-2', H-7'), 1.28 (m, 6H, H-4', H-5', H-6'), 0.97 (d, 3H, Me, J=7.5 Hz), 0.88 (d, 6H, Me, J=7.5 Hz).

EXAMPLE E10

Synthesis of 2,5-Bischloromethyl-4-methoxy-3'-(3,7-dimethyloctyloxy)biphenyl

Procedure analogous to Example E5; the product (25% yield) was obtained by distillation in a short-path still (0.2 mbar, 247° C.) as a colorless, highly viscous oil. More product could be obtained from the distillation residue by column chromatography (purity: 99%).

$^1$H NMR ($CDCl_3$): δ [ppm]=7.32 (t; 1H; J=8 Hz; H-5'), 7.30, 7.04 (2×s, 2×1H, H-3, H-6), 6.93 (m; 3H; H-2', H-4', H-6'), 4.66, 4.53 (2×s, 2×2H, $CH_2Cl$), 4.04 (m, 2H, $O-CH_2$), 3.95 (s, 3H, O—Me), 1.84 (m, 1H, H-3'), 1.60 (m, 3H, H-2', H-7'), 1.25 (m, 6H, H-4', H-5', H-6'), 0.94 (d, 3H, Me, J=7.5 Hz), 0.86 (d, 6H, Me, J=7.5 Hz).

F) Oxidations by Reaction C(a)

EXAMPLE F1

Synthesis of 2-(4'-Hexyloxyphenyl)terephthalaldehyde 70 ml of dichloromethane were placed in a reaction vessel, admixed with oxalyl chloride (8.4 g, 5.7 ml, 66 mmol) and cooled to −60° C. A solution of DMSO (10.2 g, 9.3 ml, 131 mmol) in 30 ml of dichloromethane was added dropwise to this mixture over a period of 10 minutes. The mixture was stirred for another 5 minutes. A solution of 2,5-bis(hydroxymethyl)-4'-hexyloxybiphenyl (10 g, 32 mmol) (cf. D1) in 70 ml of dichloromethane was then added dropwise over a period of 15 minutes (the reaction solution became turbid). It was stirred for another 10 minutes and triethylamine (15.9 g, 21.8 ml, 157 mmol) was subsequently added dropwise. The reaction solution became yellow during this procedure and a precipitate was formed. The acetone/dry ice bath was removed and the mixture was stirred for 2 hours at RT. A light-colored solid was then floating on the yellow liquid phase. The mixture was admixed with 150 ml of water, stirred for another 10 minutes (solid entered solution), the organic phase was separated off, the aqueous phase was extracted twice with dichloromethane, the combined organic phases were subsequently washed three times with water, dried over $Na_2SO_4$, filtered and subsequently evaporated to dryness on a rotary evaporator. The yellow oil crystallized after some time at RT and was subsequently recrystallized from hexane. It took a relatively long time for the product to become solid: pale beige, microcrystalline powder, 5.67 g (57%), purity about 98%.

Melting point: 44.5–45.5° C.; $^1$H NMR (400 MHz; $CDCl_3$): δ [ppm]=10.14 (s; 1H; 1-CHO), 10.05 (d; 1H; J=08 Hz; 4-CHO), 8.13 (d; 1H; J=7.5 Hz; H-6), 7.96 (d; 1H; J=1.5 Hz; H-3), 7.94 (ddd; 1H; $J_1$=7.7, $J_2$ 1.5, $J_3$=0.8 Hz; H-5), 7.33, 7.03 (AA'BB'; 4H; H-phenyl), 4.03 (t; 2H; J=6.7 Hz; $O-CH_2$), 1.83 (quint; 2H; J=6.6 Hz; $O-CH_2-CH_2$), 1.55–1.35 (m; 6H; H-alkyl), 0.92 (t; 3H; J=7.2 Hz; $CH_3$).

The purity of the compound is demonstrated by the $^1$H NMR spectrum shown in FIG. 3.

G. Reactions Using Reaction D

EXAMPLE G1

Synthesis of 2,5-bis(Diethylmethylenephosphonate)-4'-hexyloxybiphenyl 2,5-bis(chloromethyl)-4'-hexyloxybiphenyl (9.2 g, 26.2 mmol) (cf. E2) and triethyl phosphite (10.9 g, 11.2 ml, 65.5 mmol) were mixed under protective gas and heated to an oil bath temperature of 60° C. (without condenser). Chloroethane was given off. After a reaction time of 40 minutes, the mixture was slowly heated with a condenser and was subsequently stirred for 3 hours at 190° C. It was subsequently dried at about 1 mbar first at RT then while heating to 190° C. The crude product was taken up in ethyl acetate, extracted with water and finally again freed of solvent on a rotary evaporator: 13.11 g (90%) of pale brownish oil. Purity: about 90% ($^1$H NMR).

$^1$H NMR (400 MHz; CDCl$_3$): δ [ppm]=7.50 (dd; 1H; J$_1$=8.2, J$_2$=2.5 Hz; H-6), 7.28, 6.93 (AA'BB'; 4H; H-phenyl), 7.24 (td; 1H; J$_1$=8.2, J$_2$=2.2 Hz; H-5), 7.16 (m; 1H; H-3), 3.97 (m; 10H; P—O—CH$_2$, aryl-O—CH$_2$), 3.17, 3.13 (each: d; 2H; J=8 Hz; CH$_2$—P), 1.82 (m; 2H; O—CH$_2$—CH$_2$), 1.54–1.33 (m; 6H; H-alkyl), 1.25, 1.22 (each: t, 6H; J=6.7 Hz; P—O—CH$_2$—CH$_3$), 0.92 (m; 3H; CH$_3$).

V) Comparative Examples

EXAMPLE V1

Synthesis of 2,5-Dimethyl-4'-hexyloxybiphenyl

Bromo-p-xylene (8.3 g, 45 mmol) (cf. A1 a)), K$_2$CO$_3$ (12.4 g, 90 mmol), 70 ml of toluene and 70 ml of H$_2$O were placed in a reaction vessel and argon was passed in for 30 minutes. 4-hexyloxyphenylboronic acid (10 g, 45 mmol) and Pd(PPh$_3$)$_4$ (0.65 g, 0.56 mmol) were subsequently added under protective gas. The yellow-green, turbid mixture was stirred vigorously under a blanket of protective gas for about 20 hours at an internal temperature of 85° C. After phase separation, the organic phase was shaken with dilute HCl/H$_2$O (until neutral). The aqueous phase was shaken with toluene and the organic phases were combined. After filtering off any palladium residues, the solution was evaporated. The crude product was purified by distillation under reduced pressure: the product was obtained as a yellow oil (boiling point: 117°–125° C./0.08 mbar): 10.3 g (81%). Purity>95% ($^1$H-NMR).

$^1$H NMR (400 MHz; CDCl$_3$): δ [ppm]=7.22, 6.92 (AA'BB'; 4H; H-phenyl), 7.13 (d; 1H; J=8.2 Hz; H-6), 7.04 (m; 2H; H-3, H-5), 3.99 (t; 2H; J=7.2 Hz; O—CH$_2$), 2.33, 2.23 (each: s; 3H; aryl-Me), 1.80 (quint; 2H; J=7.0 Hz; O—CH$_2$—CH$_2$), 1.50–1.34 (m; 6H; H-alkyl), 0.92 (m; 3H; CH$_3$).

EXAMPLE V2

Attempted Synthesis of 2,5-Bisbromomethyl-4'-hexyloxybiphenyl (Using a method similar to that given in: J. Andersch et al., J. Chem. Soc. Chem. Commun. 1995, 107)

2,5-dimethyl-4'-hexyloxybiphenyl (9.05 g, 32 mmol), N-bromosuccinimide (NBS) (11.81 g, 66 mmol) and azobisisobutyronitrile (0.5 g, 3.05 mmol) together with CCl$_4$ (75 ml) were placed in a reaction vessel and refluxed for 5 days with exclusion of moisture. After two days (after checking by TLC), another equivalent of NBS was added. The solid was filtered off with suction, the precipitate was stirred once more with carbon tetrachloride and filtered off with suction; according to TLC, no product was present in the solid and the brownish mother liquor was evaporated. This gave 17.53 g (125%) of an oily crude product. According to $^1$H NMR, this comprised different halogenated compounds (both aryl-CH$_3$ groups and aryl-CHBr$_2$ groups were observed as by-products; bromination of the alkoxy chain was likewise not to be ruled out). No main product could be isolated.

What is claimed is:

1. A polymerizable biaryl derivative of the formula (I), $$\left[ \begin{array}{c} (R'')n \\ \text{Aryl} \end{array} \right] \text{Ring 2}$$

$$\left[ \begin{array}{c} X \\ Y^1 \\ (R')m \end{array} \begin{array}{c} Y^3 \\ Y^2 \\ X \end{array} \right] \text{Ring 1}$$

(I)

where the symbols and indices have the following meanings:

X: —CH$_2$Z, —CHO;

Y$^1$, Y$^2$, Y$^3$: identical or different, CH or N;

Z: identical or different, I, Cl, Br, CN, SCN, NCO, PO(OR$^1$)$_2$, PO(R$^2$)$_2$, P(R$^3$)$_3$$^+$A$^-$;

Aryl: 2-, 3- or 4-pyridinyl, 2-, 4- or 5-pyrimidinyl, 2-pyrazinyl, 3- or 4-pyridazinyl, 2-, 3-, 4-, 5-, 6-, 7- or 8-quinolyl, 2- or 3-thiophenyl, 2- or 3-pyrrolyl, 2- or 3-furanyl or 2-(1,3,4-oxadiazol)yl;

R', R'': identical or different, CN, F, Cl, a straight-chain or branched or cyclic alkyl or alkoxy group having from 1 to 20 carbon atoms, where one or more nonadjacent CH$_2$ groups is optionally replaced by —O—, —S—, —CO—, —COO—, —O—CO—, —N$_4$—, —(NR$^5$R$^6$)$^+$—A$^-$ or —CONR$^7$— and one or more H atoms is optionally replaced by F, or an aryl group having from 6 to 14 carbon atoms which may be substituted by one or more nonaromatic radicals R';

R$^1$, R$^2$, R$^3$, R$^5$, R$^6$: identical or different, aliphatic or aromatic hydrocarbon radicals having from 1 to 20 carbon atoms;

R$^4$, R$^7$: identical or different, hydrogen or aliphatic or aromatic hydrocarbon radicals having from 1 to 20 carbon atoms;

A$^-$: a singly charged anion or its equivalent;

m: 0, 1 or 2;

n: 1, 2, 3, 4 or 5.

2. A polymerizable biaryl derivative as claimed in claim 1, wherein the symbols and indices in the formula (I) have the following meanings:

X: —CH$_2$Z, CHO;

Z: Cl, Br, CN, PO(OR$^1$)$_2$, PO(R$^2$)$_2$, P(R$^3$)$_3$$^+$A$^-$;

Y$^1$, Y$^2$, Y$^3$: CH;

R': identical or different, straight-chain or branched alkoxy group having from 1 to 12 carbon atoms;

R'': identical or different, straight-chain or branched alkyl or alkoxy group having from 1 to 12 carbon atoms;

m: 0, 1;

n: 1, 2, 3.

3. A polymerizable biaryl derivative of the formula (I) as claimed in claim 1, wherein one of the groups T or T' is a perfluoroalkylsulfonate radical having from 1 to 12 carbon atoms.

4. A polymerizable biaryl derivative of the formula (I),

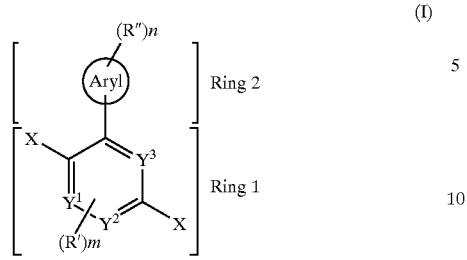

where the symbols and indices have the following meanings:
X: —CH$_2$Z, —CHO;
Y$^1$, Y$^2$, Y$^3$: are identical or different, CH or N, provided that Y$^1$, Y$^2$ and Y$^3$ are not CH at the same time,
Z: identical or different, I, Cl, Br, CN, SCN, NCO, PO(OR$^1$)$_2$, PO(R$^2$)$_2$, P(R$^3$)$_3{}^+$A$^-$;
Aryl: an aryl group having from 6 to 14 carbon atoms;
R', R'': identical or different, CN, F, Cl, a straight-chain or branched or cyclic alkyl or alkoxy group having from 1 to 20 carbon atoms, where one or more nonadjacent CH$_2$ groups is optionally replaced by —O—, —S—, —CO—, —COO—, —O—CO—, —NR$_4$—, —(NR$^5$R$^6$)$^+$—A$^-$ or —CONR$^7$— and one or more H atoms is optionally replaced by F, or an aryl group having from 6 to 14 carbon atoms which may be substituted by one or more nonaromatic radicals R';
R$^1$, R$^2$, R$^3$, R$^5$, R$^6$: identical or different, aliphatic or aromatic hydrocarbon radicals having from 1 to 20 carbon atoms;
R$^4$, R$^7$: identical or different, hydrogen or aliphatic or aromatic hydrocarbon radicals having from 1 to 20 carbon atoms;
A$^-$: a singly charged anion or its equivalent;
m: 0, 1 or 2;
n: 1, 2, 3, 4 or 5.

5. A process for preparing a polymerizable biaryl derivative of the formula (I),

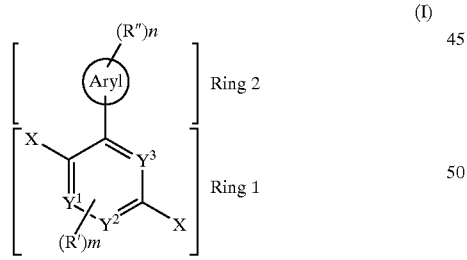

where the symbols and indices have the following meanings:
X: —CH$_2$Z, —CHO;
Y$^1$, Y$^2$, Y$^3$: identical or different, CH or N;
Z: identical or different, I, Cl, Br, CN, SCN, NCO, PO(OR$^1$)$_2$, PO(R$^2$)$_2$, P(R$^3$)$_3{}^{+A-}$;
Aryl: 2-, 3- or 4-pyridinyl, 2-, 4- or 5-pyrimidinyl, 2-pyrazinyl, 3- or 4-pyridazinyl, 2-, 3-, 4-, 5-, 6-, 7- or 8-quinolyl, 2- or 3-thiophenyl, 2- or 3-pyrrolyl, 2- or 3-furanyl or 2-(1,3,4-oxadiazol)yl;
R', R'': identical or different, CN, F, Cl, a straight-chain or branched or cyclic alkyl or alkoxy group having from 1 to 20 carbon atoms, where one or more nonadjacent CH$_2$ groups is optionally replaced by —O—, —S—, —CO—, —COO—, —O—CO—, —NR$_4$—, —(NR$^5$R$^6$)$^+$—A$^-$ or —CONR$^7$— and one or more H atoms is optionally replaced by F, or an aryl group having from 6 to 14 carbon atoms which may be substituted by one or more nonaromatic radicals R';
R$^1$, R$^2$, R$^3$, R$^5$, R$^6$: identical or different, aliphatic or aromatic hydrocarbon radicals having from 1 to 20 carbon atoms;
R$^4$, R$^7$: identical or different, hydrogen, or aliphatic or aromatic hydrocarbon radicals having from 1 to 20 carbon atoms
A$^-$: a singly charged anion or its equivalent;
m: 0, 1 or 2;
n: 1, 2, 3, 4 or 5;
which comprises
A. reacting two aryl derivatives of the formula (II) and (III),

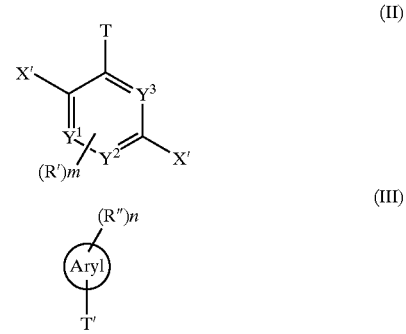

in an inert solvent in the presence of a palladium catalyst at a temperature in the range from 0° C. to 200° C. to give an intermediate of the formula (IV)

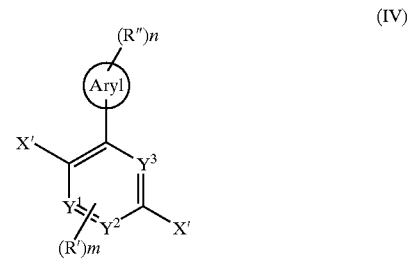

where the symbols and indices have the meanings given in formula (I) and X': CH$_2$OH or COOR$^8$;
one of the groups T or T' is Cl, Br, I or a perfluoroalkylsulfonate radical, and the other group T or T' is SnR$_3$, BQ$_1$Q$_2$, where
Q$_1$, Q$_2$ are identical or different and are each —OH, C$_1$–C$_4$-alkoxy, C$_1$–C$_4$-alkyl, phenyl which may be substituted with C$_1$–C$_4$-alkyl, C$_1$–C$_4$-alkoxy or halogen groups, or halogen or Q$_1$ and Q$_2$ together form a C$_1$–C$_4$-alkylenedioxy group which may be substituted by one or two C$_1$–C$_4$-alkyl groups; and
R$^8$ are identical or different and are each H or a straight-chain or branched alkyl group having from 1 to 12 carbon atoms;
B. if the group X' in the intermediate of the formula (IV) is COOR$^8$ (IVa), reducing this by means of a reducing agent to give an intermediate of the formula (IV) in which X' is CH$_2$OH (IVb); and C. reacting the resulting intermediate of the formula (IVb) according to one of the following reactions:
   a) selective oxidation to form a compound of the formula (I) where X=CHO, or
   b) replacement of the OH group by a halogen or pseudohalogen by means of nucleophilic substitution to form a compound of the formula (Ib)

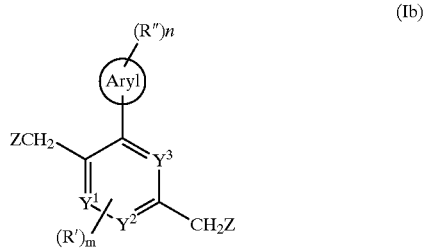

where Z=Cl, Br, I, CN, SCN, OCN; and
D. optionally, converting compounds of the formula (Ib) into a biaryl derivative of the formula (Ic)

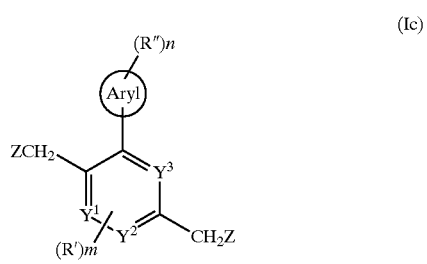

where Z=PO(OR$^1$)$_2$, PO(R$^2$)$_2$, P(R$^3$)$_3{}^+$A$^-$ by reaction with the corresponding organophosphorus compounds.

6. A process for preparing a polymerizable biaryl derivative of the formula (I) as claimed in claim 5, wherein one of the groups T or T' is a perfluoroalkylsulfonate radical having from 1 to 12 carbon atoms.

7. The process as claimed in claim 5, wherein T in the formula (II) is I, Br, Cl or a perfluoroalkylsulfonate radical having from 1 to 12 carbon atoms, and T' in the formula (III) is BQ$_1$Q$_2$, where Q$_1$, Q$_2$ are identical or different and are each —OH, C$_1$–C$_4$-alkoxy, C$_1$–C$_4$-alkyl, phenyl which may bear C$_1$–C$_4$-alkyl, C$_1$–C$_4$-alkoxy or halogen as substituents, or halogen or Q$_1$ and Q$_2$ together form a C$_1$–C$_4$-alkylenedioxy group which may be substituted by one or two C$_1$–C$_4$-alkyl groups.

8. The process as claimed in claim 5, wherein the compounds of the formula (II) and (III), a base and a palladium catalyst comprising at least one complexing ligand are added to water, one or more inert organic solvents and reacted at a temperature in the range from 50 to 150° C.

9. The process as claimed in claim 5, wherein a compound of the formula (II) in which X'=COOR$^8$ is used.

10. The process as claimed in claim 5, wherein, in step B, the intermediate formula (IV) is converted into a bisalcohol of the formula (IVb) by
   a) reaction with LiAlH$_4$, or diisobutylaluminum hydride (DIBAL-H) in tetrahydrofuran (THF) or toluene;
   b) reaction with boron hydride;
   c) reaction with hydrogen in the presence of a catalyst, or
   d) reaction will sodium or sodium hydride.

11. The process as claimed in claim 5, wherein in step Ca, the bisalcohol of the formula (IVb) is converted into a bisaldehyde of the formula (I) with X=CHO by a) oxidation using dimethyl sulfoxide/oxalyl chloride or
b) oxidation using pyridinium chlorochromate or pyridinium dichromate.

12. The process as claimed in claim 5, wherein in step Cb, the bisalcohol of the formula (IVb) is converted into a compound of the formula (Ib) in which Z is Cl or Br by
   a) reaction with HCl or HBr or
   b) reaction with thionyl chloride or thionyl bromide.

13. The process as claimed in claim 5, wherein in step D, a compound of the formula (Ib) is converted into a bisphosphonate of the formula (Ic) in which Z=—PO(R$^1$)$_2$ by reaction with a trialkyl phosphite.

14. A polymer which is obtained by a process which comprises adding at least one biaryl derivative as claimed in claim 1 as a monomer, and polymerizing the monomer.

15. An electroluminscent material which comprises a polymer as claimed in claim 14.

16. In a process for preparing a polymer, the improvement which comprises adding at least one biaryl derivative as claimed in claim 1 as a monomer, and polymerizing the monomer.

17. A process for preparing a polymerizable biaryl derivative of the formula (I),

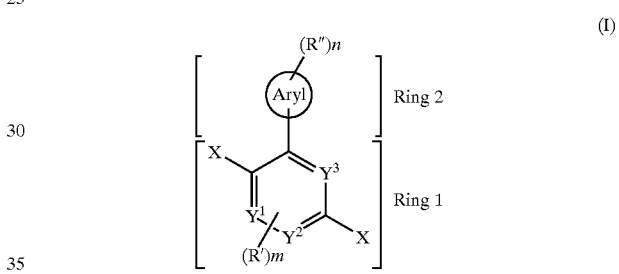

where the symbols and indices have the following meanings:
   X: —CH$_2$Z, —CHO;
   Y$^1$, Y$^2$, Y$^3$: are identical or different, CH or N, provided that Y$^1$, Y$^2$ and Y$^3$ are not CH at the same time.
   Z: identical or different, I, Cl, Br, CN, SCN, NCO, PO(OR$^1$)$_2$, PO(R$^2$)$_2$, P(R$^3$)$_3{}^+$A$^-$;
   Aryl: an aryl group having from 6 to 14 carbon atoms;
   R', R'': identical or different, CN, F, Cl, a straight-chain or branched or cyclic alkyl or alkoxy group having from 1 to 20 carbon atoms, where one or more nonadjacent CH$_2$ groups is optionally replaced by —O—, —S—, —CO—, —COO—, —O—CO—, —NR$_4$—, —(NR$^5$R$^6$)$^+$—A$^-$ or —CONR$^7$— and one or more H atoms is optionally replaced by F, or an aryl group having from 6 to 14 carbon atoms which may be substituted by one or more nonaromatic radicals R';
   R$^1$, R$^2$, R$^3$, R$^5$, R$^6$: identical or different, aliphatic or aromatic hydrocarbon radicals having from 1 to 20 carbon atoms;
   R$^4$, R$^7$: identical or different, hydrogen, or aliphatic or aromatic hydrocarbon radicals having from 1 to 20 carbon atoms
   A$^-$: a singly charged anion or its equivalent;
   m: 0, 1 or 2;
   n: 1, 2, 3, 4 or 5;
   which comprises
   A. reacting two aryl derivatives of the formula (II) and (III),

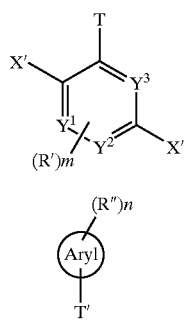

(II)

(III)

in an inert solvent in the presence of a palladium catalyst at a temperature in the range from 0° C. to 200° C. to give an intermediate of the formula (IV)

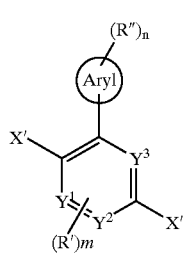

(IV)

where the symbols and indices have the meanings given in formula (I) and X': $CH_2OH$ or $COOR^8$;
one of the groups T or T' is Cl, Br, I or a perfluoroalkylsulfonate radical, and the other group T or T' is $SnR_3$, $BQ_1Q_2$, where
  $Q_1$, $Q_2$ are identical or different and are each —OH, $C_1$–$C_4$-alkoxy, $C_1$–$C_4$-alkyl, phenyl which may be substituted with $C_1$–$C_4$-alkyl, $C_1$–$C_4$-alkoxy or halogen groups, or halogen or $Q_1$ and $Q_2$ together form a $C_1$–$C_4$-alkylenedioxy group which may be substituted by one or two $C_1$–$C_4$-alkyl groups; and
  $R^8$ are identical or different and are each H or a straight-chain or branched alkyl group having from 1 to 12 carbon atoms;

B. if the group X' in the intermediate of the formula (IV) is $COOR^8$ (IVa), reducing this by means of a reducing agent to give an intermediate of the formula (IV) in which X' is $CH_2OH$ (IVb); and C. reacting the resulting intermediate of the formula (IVb) according to one of the following reactions:
  c) selective oxidation to form a compound of the formula (I) where X=CHO, or
  d) replacement of the OH group by a halogen or pseudohalogen by means of nucleophilic substitution to form a compound of the formula (Ib)

(Ib)

where Z=Cl, Br, I, CN, SCN, OCN; and
E. optionally, converting compounds of the formula (Ib) into a biaryl derivative of the formula (Ic)

(Ic)

where Z=$PO(OR^1)_2$, $PO(R^2)_2$, $P(R^3)_3^+A^-$ by reaction with the corresponding organophosphorus compounds.

* * * * *